US012440638B2

(12) United States Patent
Hammer et al.

(10) Patent No.: US 12,440,638 B2
(45) Date of Patent: Oct. 14, 2025

(54) HEADGEAR FOR RESPIRATORY INTERFACES

(71) Applicant: Fisher & Paykel Healthcare Limited, Auckland (NZ)

(72) Inventors: Jeroen Hammer, Auckland (NZ); Charles Nicolson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1062 days.

(21) Appl. No.: 17/477,376

(22) Filed: Sep. 16, 2021

(65) Prior Publication Data

US 2022/0001128 A1 Jan. 6, 2022

Related U.S. Application Data

(63) Continuation of application No. 15/300,237, filed as application No. PCT/IB2015/052350 on Mar. 31, 2015, now Pat. No. 11,160,945.

(60) Provisional application No. 61/973,069, filed on Mar. 31, 2014.

(51) Int. Cl.

| | |
|---|---|
| ***A61M 16/00*** | (2006.01) |
| ***A44B 18/00*** | (2006.01) |
| ***A61M 16/06*** | (2006.01) |

(52) U.S. Cl.
CPC ..... *A61M 16/0683* (2013.01); *A61M 16/0688* (2014.02); *A61M 2205/0216* (2013.01)

(58) Field of Classification Search
CPC ...... A44B 18/0069; A44B 18/00; Y10T 24/27
See application file for complete search history.

(56) References Cited

U.S. PATENT DOCUMENTS

| | | | | |
|---|---|---|---|---|
| 3,372,438 | A * | 3/1968 | Rinecker | D03D 27/00 224/901.4 |
| 3,747,171 | A * | 7/1973 | Montague, Jr. | A44C 5/2071 24/442 |
| 5,188,101 | A | 2/1993 | Tumolo | |
| 5,222,765 | A * | 6/1993 | Pileggi | B42F 13/0026 402/80 R |
| 5,303,428 | A | 4/1994 | Pernicka | |
| 6,470,886 | B1 | 10/2002 | Jestrabek-Hart | |
| 7,708,017 | B2 | 5/2010 | Davidson et al. | |
| 8,096,300 | B2 * | 1/2012 | Russo | A61M 16/0497 128/207.14 |
| 2002/0096176 | A1 | 7/2002 | Gunaratnam | |
| 2003/0051732 | A1 | 3/2003 | Smith et al. | |
| 2003/0196656 | A1 | 10/2003 | Moore | |

(Continued)

FOREIGN PATENT DOCUMENTS

| | | |
|---|---|---|
| AU | 2012201085 | 3/2012 |
| EP | 1 902 743 A1 | 3/2008 |

(Continued)

OTHER PUBLICATIONS

International Search Report and Written Opinion, PCT/1B2015/052350, dated Jun. 25, 2015, 15 pp.

*Primary Examiner* — Jack W Lavinder
(74) *Attorney, Agent, or Firm* — VIA LLP

(57) ABSTRACT

Several embodiments of straps and headgear assemblies are described. Some of the embodiments provide straps that can had varied elasticity over the length of the straps. Some of the embodiments provide adjustment mechanisms that facilitate customization of headgear to a user.

20 Claims, 32 Drawing Sheets

(56) References Cited

U.S. PATENT DOCUMENTS

| | | | | |
|---|---|---|---|---|
| 2007/0215161 | A1 | 9/2007 | Frater | |
| 2008/0244875 | A1 | 10/2008 | Chou | |
| 2012/0067351 | A1 | 3/2012 | MacMillan | |
| 2012/0132209 | A1 | 5/2012 | Rummery | |
| 2012/0138063 | A1 | 6/2012 | Eves | |
| 2012/0199131 | A1 | 8/2012 | Sofranko et al. | |
| 2014/0000070 | A1* | 1/2014 | Ashraf .................. | A61F 13/625 24/448 |
| 2014/0173944 | A1* | 6/2014 | Dromms ............ | A43C 11/1493 24/442 |
| 2017/0182276 | A1 | 6/2017 | Hammer et al. | |

FOREIGN PATENT DOCUMENTS

| | | | |
|---|---|---|---|
| EP | 2000168 | A1 | 12/2008 |
| EP | 2022528 | A2 | 2/2009 |
| EP | 2 130 563 | | 12/2009 |
| GB | 2453101 | | 4/2009 |
| WO | 2008070929 | A1 | 6/2008 |
| WO | 2009038918 | | 3/2009 |
| WO | 2010066004 | A1 | 6/2010 |
| WO | WO 11/155147 | | 12/2011 |
| WO | 20120143822 | | 10/2012 |
| WO | WO 2013/050920 | A1 | 4/2013 |
| WO | 2013128324 | A2 | 9/2013 |
| WO | WO 2013/175409 | A1 | 11/2013 |
| WO | 2014020469 | A1 | 2/2014 |
| WO | WO 14/025267 | | 2/2014 |
| WO | WO 2014/020169 | A1 | 2/2014 |
| WO | WO 14/175752 | | 10/2014 |

* cited by examiner

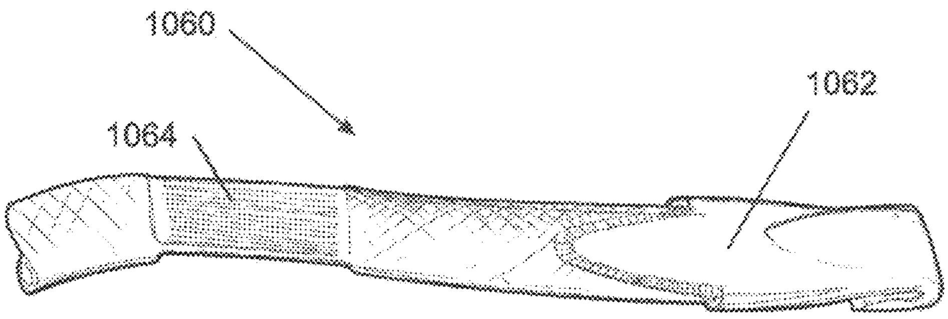
Figure 12
Figure 13
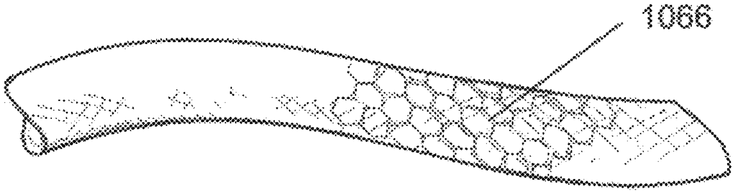
Figure 14
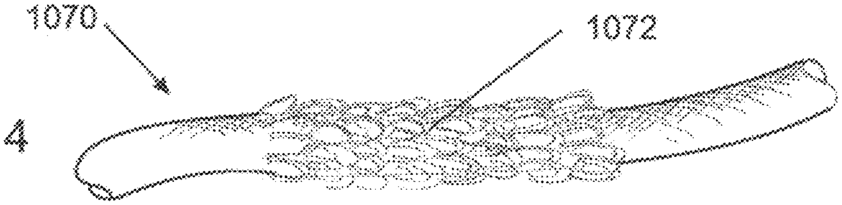
Figure 15a
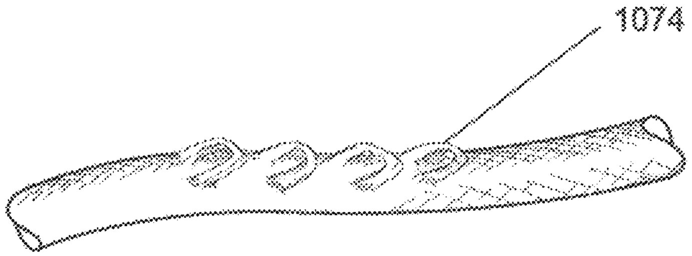
Figure 15b
Figure 16
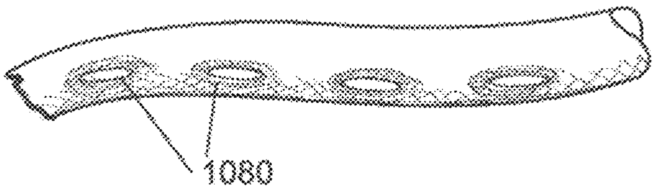

Headgear A

Headgear B

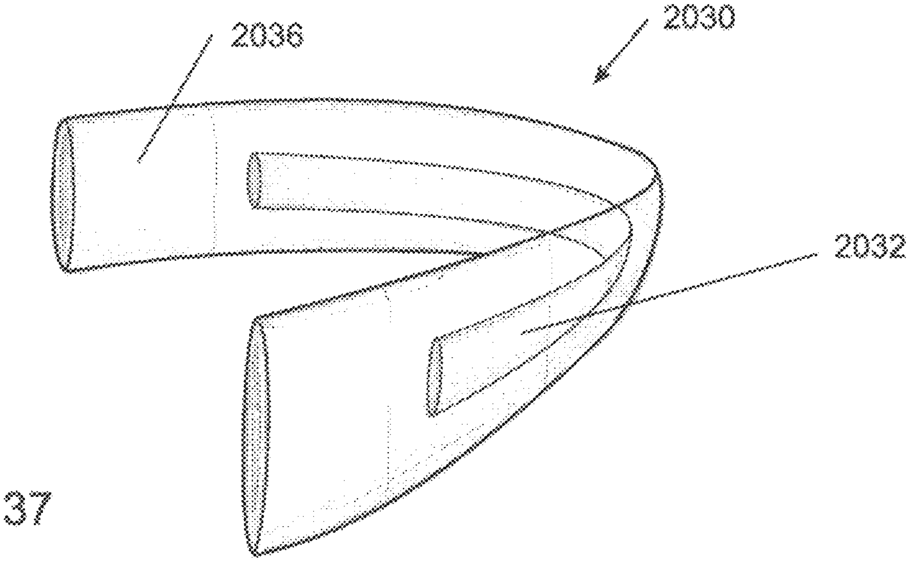
Figure 37
Figure 38a
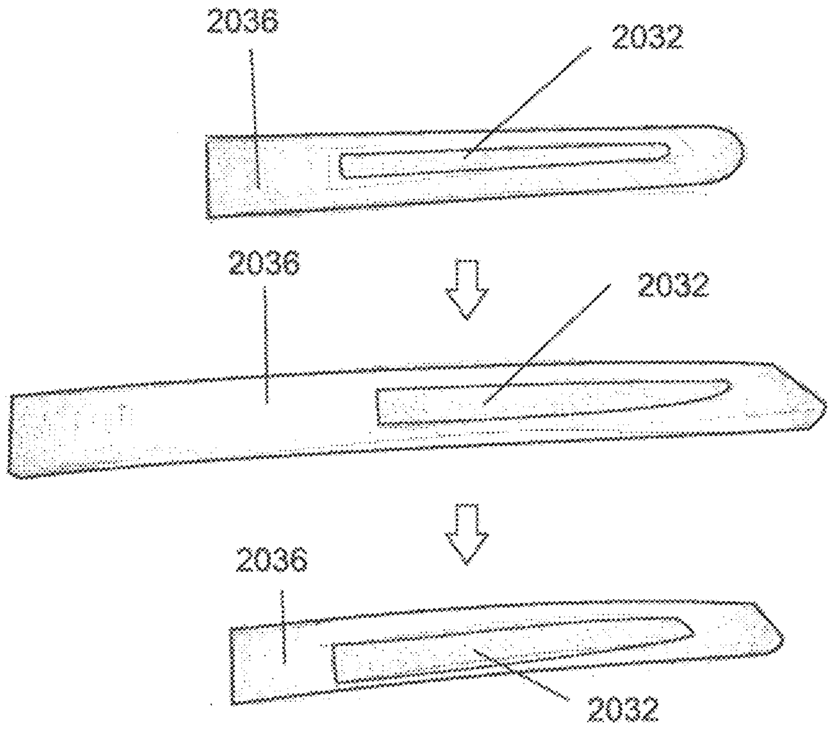
Figure 38b
Figure 38c

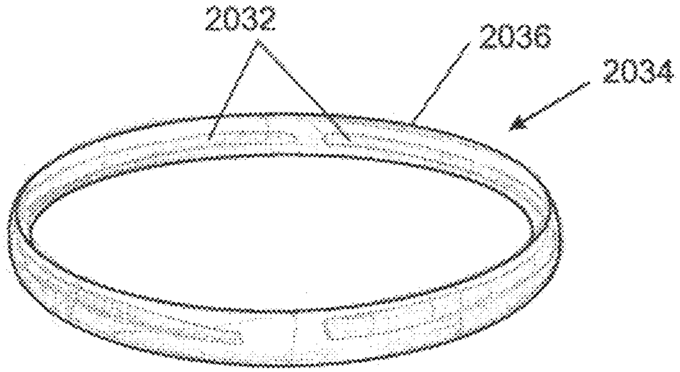
Figure 39
Figure 40
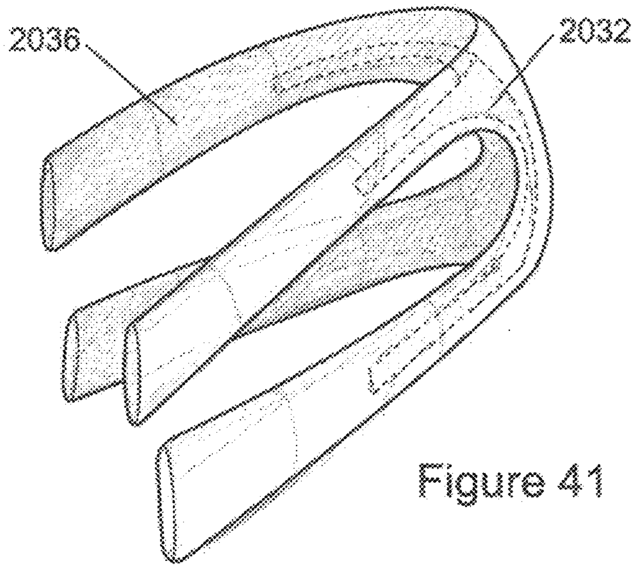
Figure 41
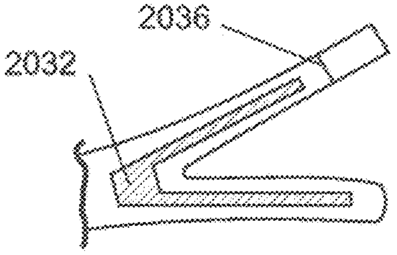
Figure 42
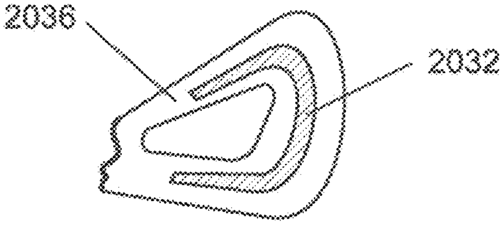
Figure 43
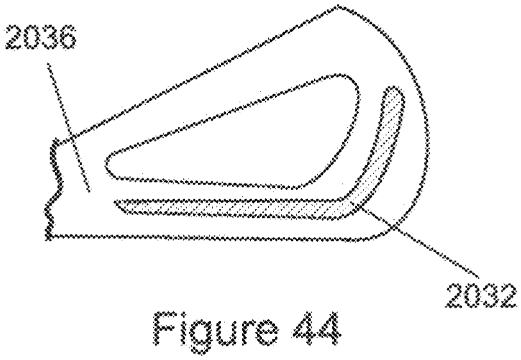
Figure 44

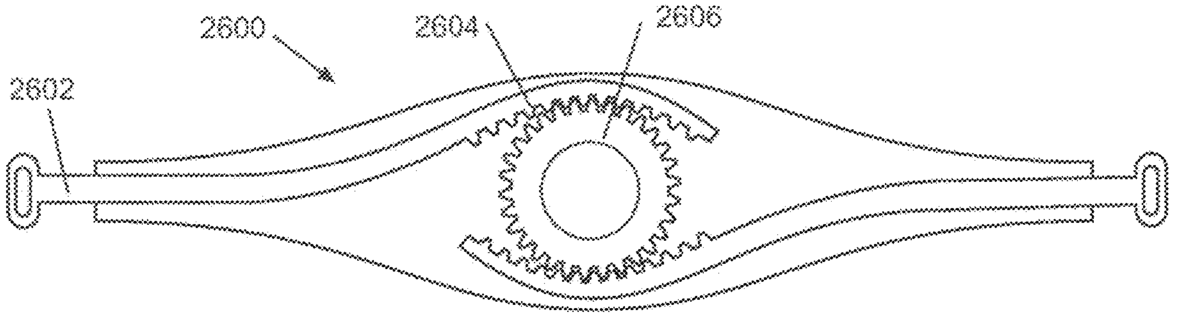
Figure 88
Figure 89
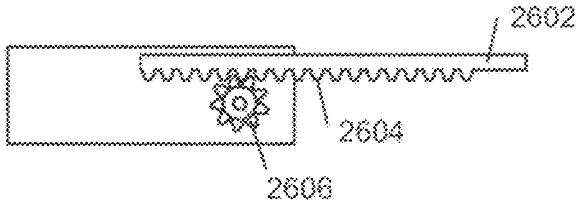
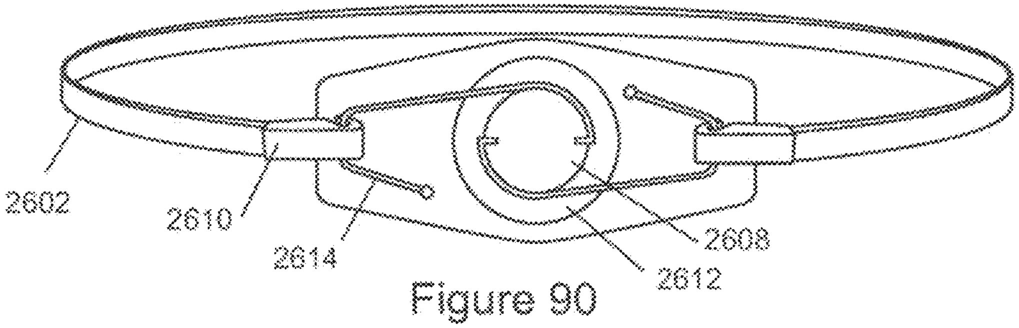
Figure 90
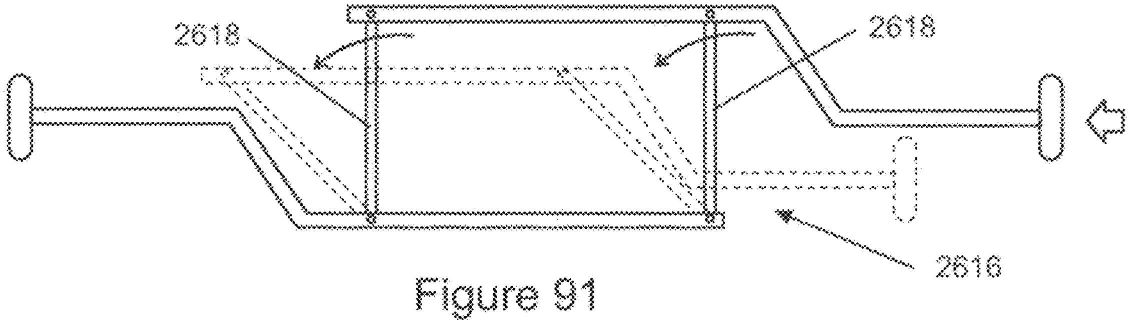
Figure 91
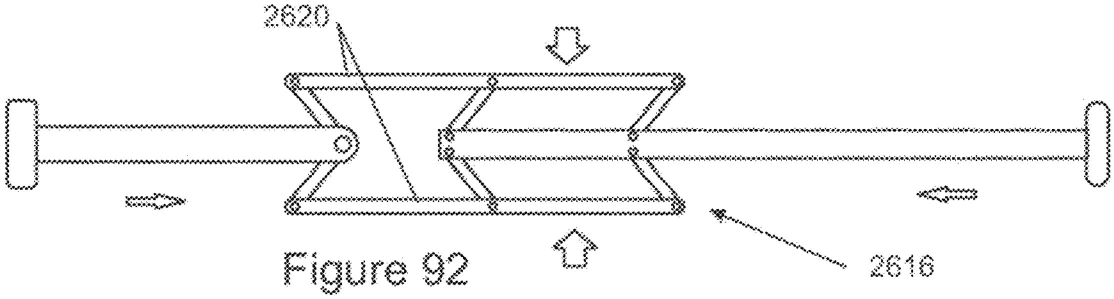
Figure 92

Figure 103
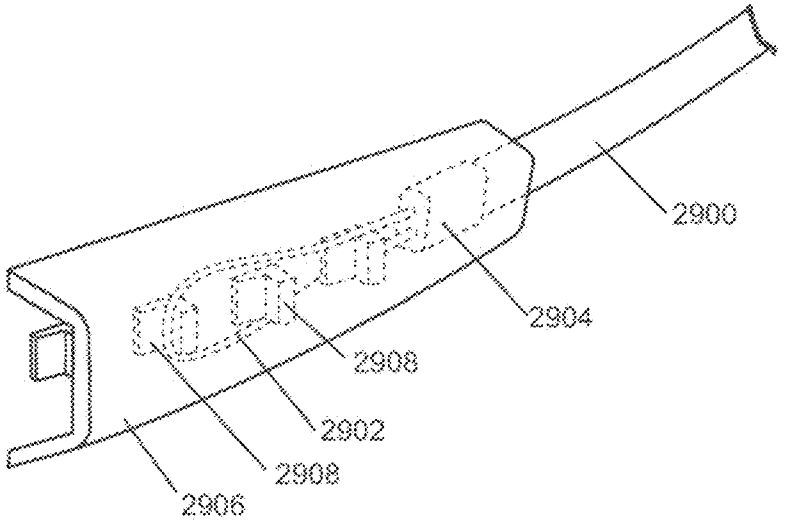
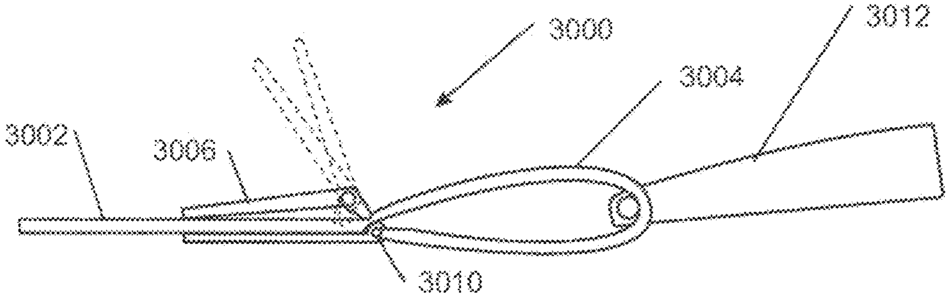
Figure 104
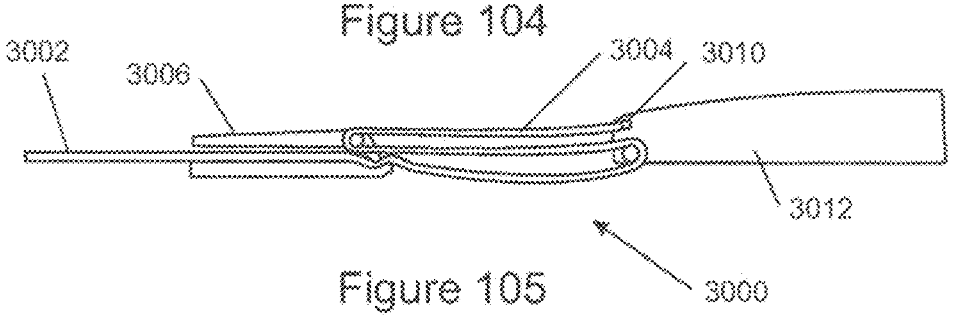
Figure 105
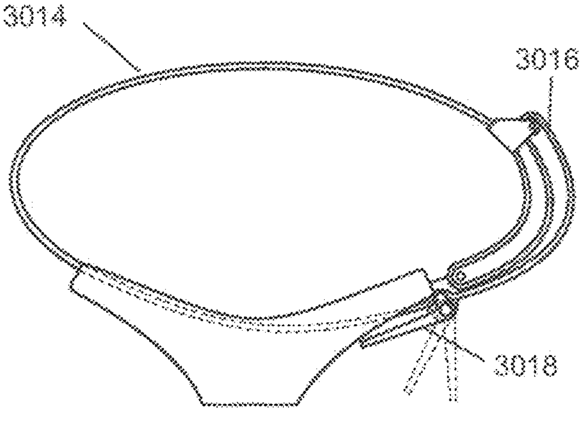
Figure 106
Figure 107a
Figure 107b
Figure 107c Figure 115
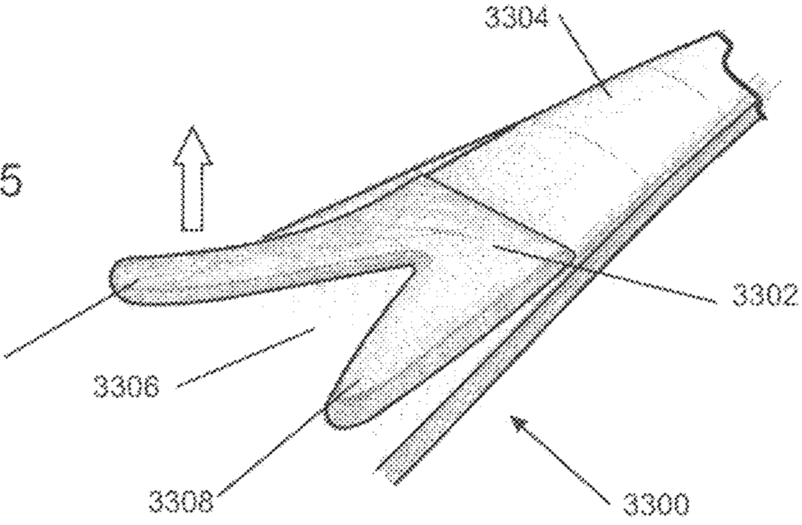
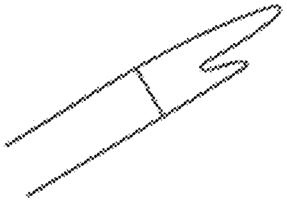
Figure 116a
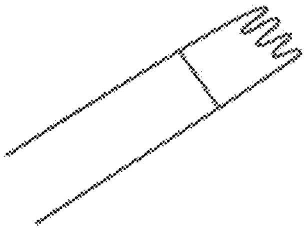
Figure 116b
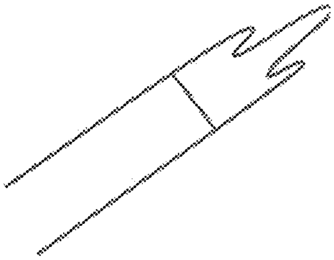
Figure 116c
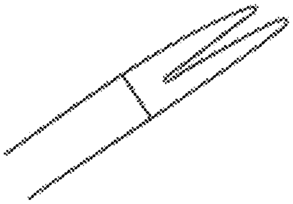
Figure 116d
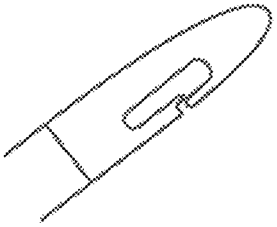
Figure 116e
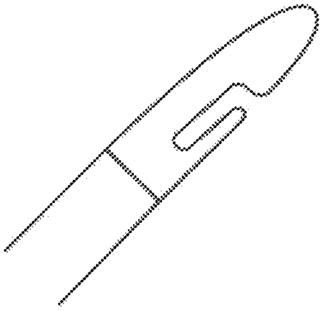
Figure 116f
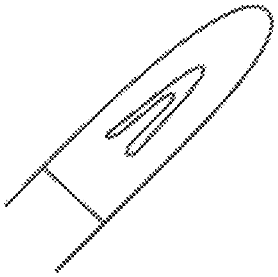
Figure 116g
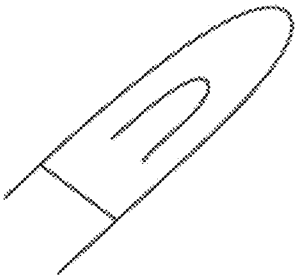
Figure 116h
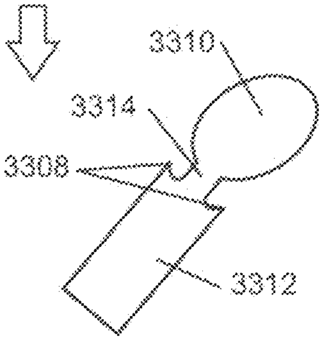
Figure 116i

HEADGEAR FOR RESPIRATORY INTERFACES

BACKGROUND

Incorporation by Reference to any Priority Applications

Any and all applications for which a foreign or domestic priority claim is identified in the Application Data Sheet as filed with the present application are hereby incorporated by reference under 37 CFR 1.57.

Field of the Invention

The present disclosure generally relates to headgear for respiratory interfaces. More particularly, the present disclosure relates to straps and hook assemblies for such headgear.

Description of the Related Art

Headgear is used to secure user interfaces during breathing treatments. Improvements to the headgear are desired to provide easier to use headgear as well as more comfortable headgear.

SUMMARY

Accordingly, a variety of configurations are shown and described herein that will provide improved fit, form and/or function to headgear and/or that will provide the public with a useful option.

In some configurations, headgear for a breathing interface is provided. The headgear comprises at least the one strap with the at least one strap having a customizable stretch characteristic.

In some configurations, the at least one strap includes at least one receiving region that is configured to receive an insert, the insert being rigid or semi-rigid.

In some configurations, the insert is removable from the receiving region.

In some configurations, the insert is movable among two or more of the at least one receiving regions. In some such configurations, wherein the insert can be replaced by a second insert that is receivable within the receiving region.

In some configurations, the at least one strap includes multiple separable segments. In some such configurations, the multiple separable segments are positioned internally within the at least one strap. In some such configurations, two adjacent segments of the multiple separable segments are configured to be dislocated from each other to provide a custom stretch characteristic in one or more locations.

In some configurations, the at least one strap incorporates a stretch component, a relatively non-stretch member and two or more buckles that interconnect the at least one strap and the relatively non-stretch member. In some such configurations, the stretch component has a greater length than the relatively non-stretch member. In some such configurations, the two or more buckles are adjustable along a length of the relatively non-stretch member. In some such configurations, the two or more buckles are adjustable such that an intermediate length of the stretch component disposed between the two buckles can be varied. In some such configurations, adjusting the spacing between the two or more buckles adjusts the amount of the stretch component that is secured to the relatively non-stretch member and, therefore, unable to stretch. In some such configurations, the relatively non-stretch component comprises a hollow portion through which the stretch component passes. In some such configurations, the two or more buckles attach to the non-stretch component with the stretch component being secured within the non-stretch component.

In some configurations, the at least one strap incorporates a stretch component, a relatively non-stretch member and two or more limiters that interconnect the at least one strap and the relatively non-stretch member. In some such configurations, the stretch component has a greater length than the relatively non-stretch member. In some such configurations, the nonstretch member comprises two or more apertures that receive the two or more limiters and the stretch member comprises two or more apertures. In some such configurations, the nonstretch member comprises at least three openings and the stretch component comprises at least three openings. In some such configurations, the two or more apertures of the non-stretch member have a first spacing and the two or more apertures of the stretch member have a second spacing. In some such configurations, the second spacing is the same as the first spacing. In some such configurations, the second spacing is different from the first spacing. In some such configurations, the second spacing is less than the first spacing. In some such configurations, the two or more limiters are connected for movement. In some such configurations, a hinge connects two adjacent limiters such that depressing one causes a lifting of the other.

In some configurations, a connector is configured to the attached to the at least one strap and the connector comprises a passage through which the at least one strap passes. In some such configurations, the connector comprises a clamping configuration that secures the connector in position along the at least one strap. In some such configurations, the clamping configuration comprises a living hinge between a first portion and a second portion of the connector and the first portion can be brought into engagement with the second portion with the connector positioned in a desired location along the at least one strap. In some such configurations, the clamping configuration comprises a locking mechanism that can be provided as part of the connector. In some such configurations, the locking mechanism includes a push-button that can lock the connector in position along the at least one strap. In some such configurations, the locking mechanism includes a hinge system that locks onto the at least one strap.

In some configurations, at least a portion of the at least one strap comprises a thermoplastic element. In some such configurations, the at least one strap comprises a woven or braided construction that integrates the thermoplastic element. In some such configurations, the at least one strap can be provided with regions of different stretch characteristics through the use of ultrasonic welding. In some such configurations, one or more connectors can be attached to the at least one strap in a region that has undergone forming.

In some configurations, the headgear features upper straps, lower straps and a top strap. In some such configurations, the headgear comprises a three dimensional shape when not being worn such that the headgear does not lie flat when not being worn.

In some configurations, the headgear can be used with a patient interface.

In some such configurations, the patient interface is selected from the group consisting of full face mask, nasal mask, nasal pillows, non-invasive or a cannula. In some such configurations, the headgear and the patient interface are connected by connectors. In some such configurations, the connectors comprise clips. In some configurations, the interface comprises a delivery conduit. In some such configurations, the delivery conduit is connected to the interface with a ball joint, which may be removable. In some such configurations, the delivery conduit comprises a swivel connector. In some such configurations, the interface comprises a frame and a cushion that is removable from the frame. In some such configurations, the interface further comprises an anti-asphyxiation valve. In some such configurations, the interface further comprises bias flow holes. In some such configurations, the interface further comprises a forehead support. In some such configurations, the patient interface does not comprise a forehead support.

In some configuration, a headgear assembly is provided for use with a patient interface. The headgear assembly comprises at least one strap. The at least one strap comprises an end with a hook component. The hook component is securable to a loop component. The hook component comprises at least two fingers that are spaced apart from each other by a gap such that lifting one of the at least two fingers will not result in lifting of the other of the at least two fingers.

In some configurations, the two or more fingers are symmetrical with each other.

In some configurations, the two or more fingers are asymmetrical with each other.

In some configurations, the gap results in the at least two fingers defining a forked configuration.

In some configurations, the gap is centrally positioned along the hook component.

In some configurations, one of the at least two fingers at least partially surrounds another of the at least two fingers. In some such configurations, one of the at least two fingers completely surrounds another of the at least two fingers. In some such configurations, one of the at least two fingers defines a central tab and another of the at least two finger defines an outer tab that circumscribes the central tab.

In some configurations, one of the at least two fingers only partially surrounds another of the at least two fingers.

In some configurations, the gap extends inwardly from a lateral edge of the hook component. In some such configurations, a second gap extends inwardly from a second lateral edge of the hook component and two fingers are defined with a narrow section connecting to a wide end.

In some such configurations, the at least one strap comprises a single strap.

In some such configurations, the at least one strap comprises an upper strap and a lower strap.

In some such configurations, the at least one strap comprises an upper strap, a lower strap and a crown strap.

In some configurations, a strap is provided for a breathing assistance apparatus interface. The strap comprises a first portion and a second portion that combine to form a hollow tubular configuration. The first portion has different properties from the second portion at the same axial location along the strap.

In some such configurations, the first portion is an outer portion and the second portion is an inner portion and the outer portion has greater rigidity than the inner portion.

In some configurations, a strap is provided for a breathing assistance apparatus interface. The strap comprises a continuous braid section wherein the continuous braid section comprises a first portion and a second portion that are at differing axial positions along the continuous braid section. The first portion being relatively more stretchable than the second portion.

In some such configurations, the continuous braid section comprises a third portion with the first portion being positioned between the second portion and the third portion and the first portion being relatively more stretchable than the third portion. In some such configurations, the first portion, the second portion and the third portion define zones to secure a beaded member.

In some configurations, a strap is provided for a breathing assistance apparatus interface. The strap is formed by at least one of weaving and braiding. The strap incorporates at least one of a thermoplastic string, a rubberized string, a silicone string and a closure structure formed during the at least one of weaving and braiding. The closure structure comprises at least one of a looped surface, a well-defined loop and a button hole.

In some configurations, a strap is provided for a breathing assistance apparatus interface. The strap is formed by at least one of weaving and braiding. The strap has a varied cross section.

In some such configurations, the varied cross section comprises a window formed during the at least one of weaving and braiding.

In some such configurations, the window can be severed to form portions of two different headgear.

In some such configurations, the strap is severed between two different windows to form two different headgear.

In some such configurations, the window is filled with a mesh material.

In some such configurations, the strap forms an entire seamless headgear unit.

In some configurations, a strap is provided for a breathing assistance apparatus interface. The strap comprises a tubular component formed by at least one of braiding and weaving with a rigid or semi-rigid component being positioned within a lumen defined by the tubular component.

In some such configurations, the rigid or semi-rigid component spans a connection between a first finger of the strap and a second finger of the strap such that the rigid or semi-rigid component spans a corner between the first finger and the second finger.

In some configurations, a strap is provided for a breathing assistance apparatus. The strap comprises a stretch increasing configuration. The stretch increasing component is configured to allow increased stretchability of the strap by severing a connection between two or more adjacent portions of the strap.

In some configurations, headgear is provided for a breathing assistance apparatus. The headgear comprises a strap and a strap adjustment mechanism.

In some such configurations, the strap adjustment mechanism comprises at least one of a tie down system and at least two structures that connect a relatively nonstretch component to a relatively stretchable component in at least two corresponding spaced apart locations, wherein at least one of the at least two corresponding spaced apart locations can be adjusted relative to the other of the two locations. In some such configurations, the strap adjustment mechanism comprises a passage through a hook, the hook being used to secure the strap to the interface. In some such configurations, the strap adjustment mechanism comprises a winding mechanism. In some such configurations, the headgear further comprises an adjustment mechanism that alters a position of a mask relative to the headgear. In some such configurations, the strap adjustment mechanism comprises at least one of a pinching lever, a loop and a post connection. In some such configurations, the strap adjustment mechanism comprises at least one scissor mechanism. In some such configurations, the strap adjustment mechanism comprises a hook member and a loop fastener member, the hook member comprising a plurality of fingers.

BRIEF DESCRIPTION OF THE DRAWINGS

Certain features, aspects and advantages of specific embodiments and modifications of the present disclosure will become apparent to those skilled in the art from the detailed description herein having reference to the sheets of figures that follow.

FIG. 12 is a plan view of a strap.

FIG. 13 is a plan view of another strap.

FIG. 14 is a plan view of a strap.

FIG. 15*a* is a plan view of another strap.

FIG. 15*b* is a view of the strap of FIG. 15*a* and a connecting hook.

FIG. 16 is plan view of another strap.

FIGS. 37-46 illustrate headgear with rigid or semi-rigid components.

FIGS. 88-92 illustrate a rack and pinion adjustment for headgear and/or a mask seal.

FIG. 103 illustrates a hook adjustment for headgear and/or a mask seal.

FIGS. 104-107*c* illustrate an over-center pinch adjustment for a strap.

FIGS. 115-1161 illustrate hook and loop fastener adjustments for headgear.

DETAILED DESCRIPTION OF SPECIFIC EMBODIMENTS

Figure 1:
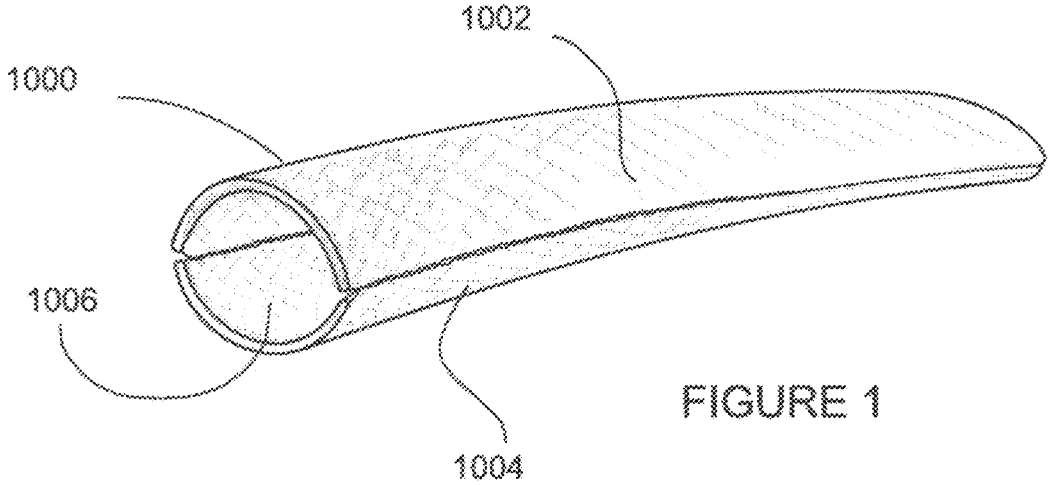
FIG. 1 is a perspective view of a portion of a strap.
Figure 2:
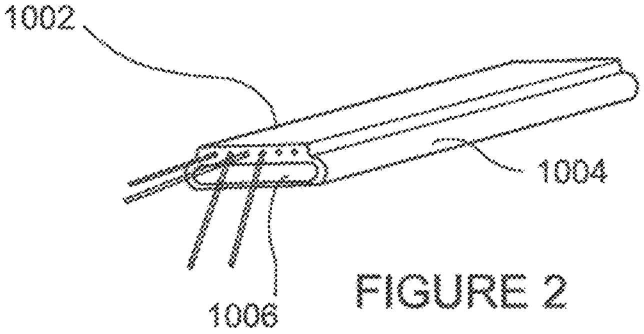
FIG. 2 is a perspective view of a portion of another strap.

In some of the following description, materials are formed using one or more of weaving, knitting and braiding. Weaving is interlacing, usually at right angles, of two sets of threads to form cloth, rug or other types of woven textiles. In automated processes, two distinct sets of yarns called the warp and the filling or weft are interlaced with each other to form a fabric. The lengthwise yarns that run front to back in the loom are called the warp while the yarns that extend crosswise are called the weft. Typically, the warp threads are held stationary while the weft threads are woven through them.

The yarn in knitted fabrics follows a meandering path, forming symmetric loops or stitches. When the interlocking loops run lengthwise, each row is called a wale. A wale can be compared with the warp in weaving. When the loops run across the fabric, each row is called a course. A course corresponds to the weft. There are two major varieties of knitting: weft knitting and warp knitting. In weft knitting, one continuous yarn forms courses across the fabric. In warn knitting, a series of yarns form wales in the lengthwise direction of the fabric. As used herein, knitting will typically refer to warn knitting but may refer to weft knitting in certain configurations.

In braiding, three or more strands can be interwoven to form a rope-like member. The interweaving is performed in a diagonally overlapping pattern. Braiding is done by intertwining yarns in whatever direction suited to the manufacturer's purpose. Braiding can be classified as two and three-dimensional braiding. Two-dimensional braid structure can be a circular or flat braid. They are formed by crossing a number of yarns diagonally so that each yarn passes alternately over and under one or more of the others. Three dimensional braiding is a two dimensional array of interconnected 2-D circular braids. As used herein, braiding will typically refer to two-dimensional braiding but could refer to three-dimensional braiding in certain configurations.

Various head strap configurations and headgear configurations will be described. In some configurations, the headgear features upper straps, lower straps and a top strap. In some such configurations, the headgear comprises a three dimensional shape when not being worn such that the headgear does not lie flat when not being worn. In some configurations, the headgear can be used with a patient interface. In some such configurations, the patient interface is selected from the group consisting of full face mask, nasal mask, nasal pillows, non-invasive or a cannula. In some such configurations, the headgear and the patient interface are connected by connectors. In some such configurations, the connectors comprise clips. In some configurations, the interface comprises a delivery conduit. In some such configurations, the delivery conduit is connected to the interface with a ball joint, which may be removable. In some such configurations, the delivery conduit comprises a swivel connector. In some such configurations, the interface comprises a frame and a cushion that is removable from the frame. In some such configurations, the interface further comprises an anti-asphyxiation valve. In some such configurations, the interface further comprises bias flow holes. In some such configurations, the interface further comprises a forehead support. In some such configurations, the patient interface does not comprise a forehead support.

Multi-Yam Knits with Split Materials

With reference now to FIGS. 1-5, a head strap configuration 1000 is shown that can be formed by braiding multiple yarns together. In some embodiments, the head strap configuration 1000 can be formed of a braid of knit components. In other words, multiple yarns can be knit together to define a knit component and then the knit component can be used to form the braid. In some embodiments, the head strap configuration 1000 can feature a split material construction in which different yarns are used for a top portion 1002 of the head strap configuration 1000 and a bottom portion 1004 of the head strap configuration 1000. The top portion 1002 and the bottom portion 1004 of the head strap configuration 1000 can be joined in any suitable manner. For example, the two may be joined by thermal bonding, stitching, adhesive or the like.

In some configurations, the knit or braid, although mainly circular and continuous, can have very different properties for the top portion 1002 (i.e., a portion other than the portion that will sit closest to the face and/or the portion furthest from the portion that will sit closest to the face) and the bottom portion 1004 (i.e., the portion that will sit closest to the face). In such configurations, the yarns or materials chosen for the top and bottom surfaces or portions 1002, 1004 can be chosen for desired properties. For example, in some configurations, one portion (e.g., the top portion 1002) may comprise a rather rigid structural side while the other portion (e.g., the bottom portion 1004) may comprise a soft, cushioning side with the soft side being the side that will be in contact with the skin. In some configurations, a strong, stiff yarn can be used to create structural rigidity for the head strap configuration 1000. In some configurations, a yarn can be used for the soft side that provides breathability and moisture absorption for the surface that will contact the skin of the user. In some configurations, such a material can include merino wool.

Figure 3:
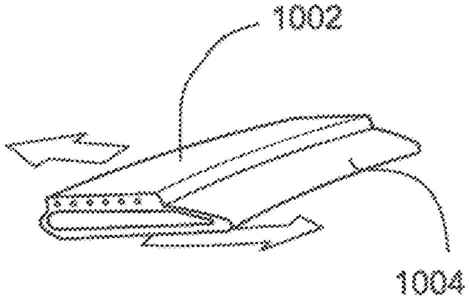
FIG. 3 is a perspective view of the strap of FIG. 2 undergoing rolling movement.

As illustrated, the strong, stiff side (e.g., the top portion 1002) can provide some structural integrity to the head strap configuration 1000. For example, the strong, stiff side can provide structural rigidity, which can help reduce or eliminate the likelihood of twisting and tangles in headgear, which can be formed using the head strap configuration 1000. Nevertheless, in the illustrated configuration, the braid resulting from the knit product would create a hollow tube that can allow some rolling of the strap relative to the user without undue slippage relative to the user, which slippage could cause chaffing over time. In other words, the head strap configuration 1000 comprises an inner lumen 1006. The inner lumen 1006 may allow relative movement between the upper portion 1002 and the lower portion 1004 without necessarily creating significant movement between the lower portion 1004 and skin or hair of the user, as shown in FIG. 3.

Figure 4:
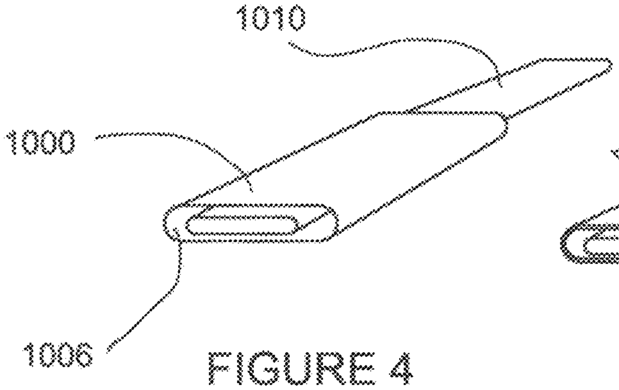
FIG. 4 is a perspective view showing a portion of a strap disposed around a structural component.
Figure 5:
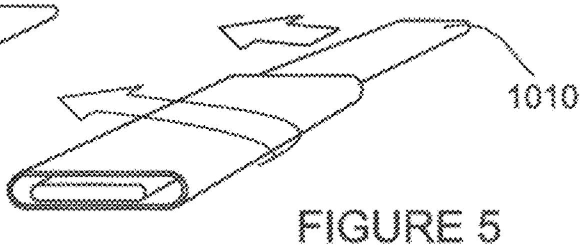
FIG. 5 is a perspective view of the strap of FIG. 4 undergoing rolling movement.

In some configurations, such as those shown in FIGS. 4 and 5, a structural headgear component 1010 can be enveloped or at least partially enveloped within the lumen 1006 of the hollow braid. For example, in the illustrated configuration, the hollow braid of the head strap configuration 1000 would be able to roll around the structural headgear component 1010 and provide softness or a soft hand to the structural headgear component 1010. In some such configurations, the hollow braid would have the same properties around the circumference of the hollow braid, which is different from the configuration discussed directly above in which an inner surface and an outer surface might have differing properties. In some configurations, however, the hollow braid also could have differing properties in different regions.

An advantage of these combined braid/knit configurations is the ability to produce the head strap during a single manufacturing process. For example, in some configurations, the knit can be built with multiple yarns and possibly very different knitting patterns for the top and the bottom half. If one of the sides is intended to be in contact with the skin, properties like breathability might be considered. One particularly interesting combination is a combination of a knit (e.g., such as the strap used with the PILAIRO interface) and a braid (e.g., a climbing rope's outer sleeve).

Multi-Yam Knit in a Continuous Braid with Sections Having Different Properties

Figure 6:
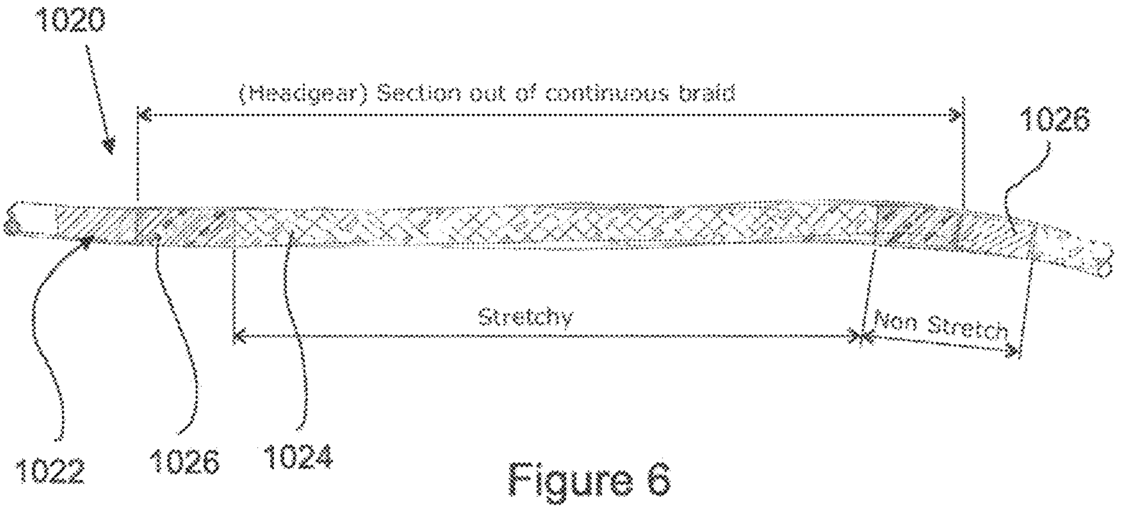
FIG. 6 is plan view of a strap having bands of different elasticity.
Figure 7:
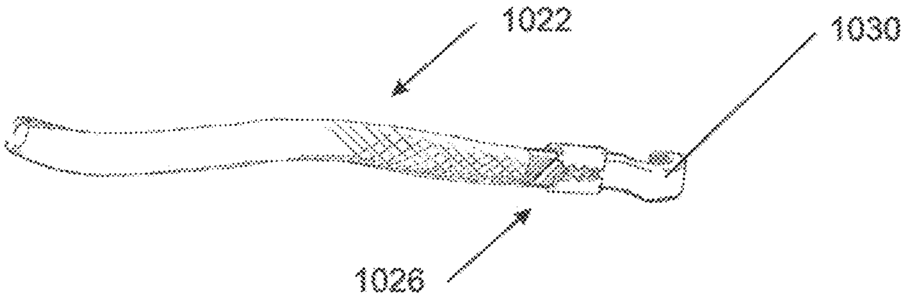
FIG. 7 is a plan view of an end connector attached to a strap having regions of differing elasticity along a length of the strap.
Figure 8:
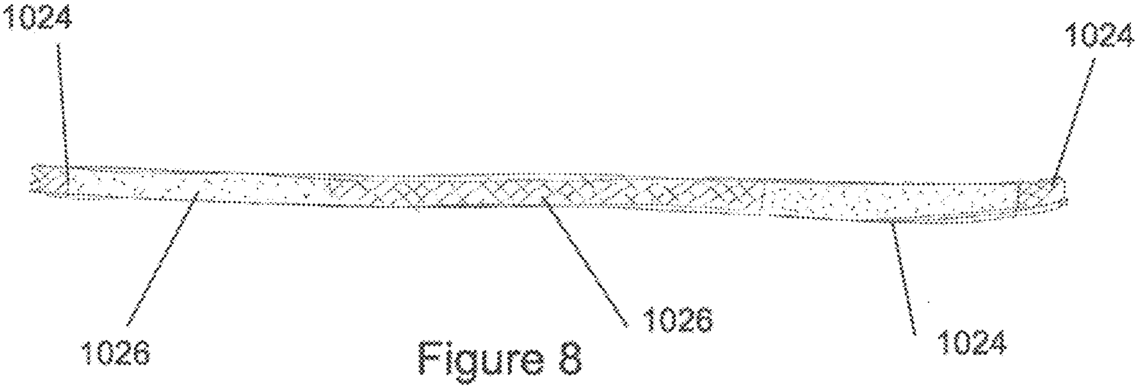
FIG. 8 is a plan view of another strap having bands of different elasticity.

With reference now to FIGS. 6-8, a head strap configuration 1020 can include a strap 1022 that combines bands 1024 with different properties. For example, the strap 1022 can be knit from multiple yarns. In such configurations, bands 1024, 1026 can be formed by primarily knitting and/or braiding with one of the yarns (e.g., relatively non-stretch yarn) where the other(s) (e.g., relatively stretch yarn) is just carried across to the next section where the roles are reversed.

In the illustrated configuration, a relatively stretchy material can be used for the strap 1022 and the relatively stretchy material can be alternated with a relatively non-stretchy material for the ends 1026. In other words, a region 1024 can be formed predominantly using a relatively stretchy yarn (i.e., a region knitted from the relatively stretchy yarn) and that region can be bounded by two regions 1026 formed predominantly using a relatively less stretchy or more rigid yarn. The number, size and configuration of the bands 1024, 1026 can be varied in any suitable or desired manner.

The relatively non-stretch regions 1026 can form ends 1026. The relatively non-stretch ends 1026 can improve the reliability of crimped connections 1030. For example, as shown in FIG. 7, when clips 1030 are crimped onto the strap 1022 (e.g., hooks or the like), the clips 1030 are more securely attached in regions that are generally less stretchy or that are more stable and less elastic in an axial direction.

Configurations featuring different regions or bands can provide increased reliability and can provide ease of manufacture. Accordingly, such configurations may result in less rejects during manufacturing options and also may result in less returns.

Multi-Yam Knits with Sections Having Different Stretch for Adjustment

Figure 9:
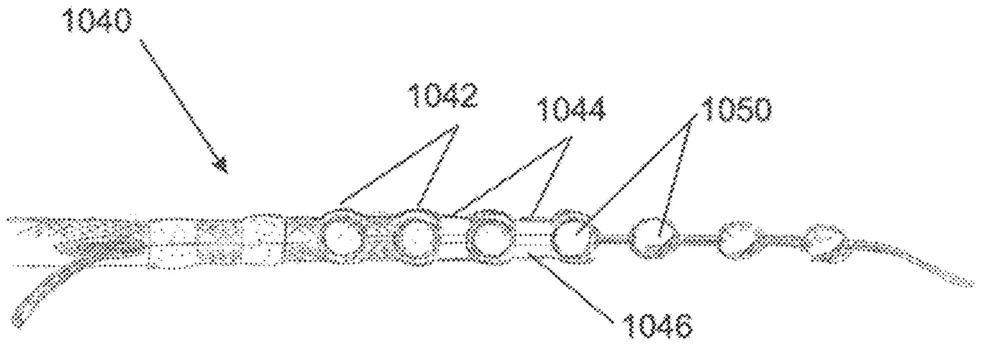
FIG. 9 is a plan view of a strap and adjustment mechanism shown in partial section.
Figure 10:
FIG. 10 is a plan view of another strap and adjustment mechanism shown in partial section.
Figure 11:
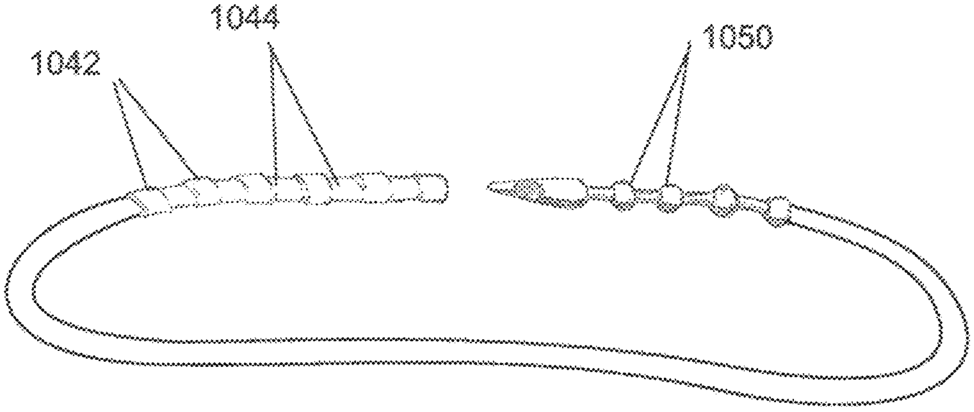
FIG. 11 is a view of a strap shown prior to connection of two ends.

With reference now to FIGS. 9-11, in some configurations, the knit of a head strap 1040 can be built using multiple yarns. In some configurations, the head strap 1040 can be formed with alternating bands 1042, 1044 of more and less elasticity. As described above, the bands 1042, 1044 can be formed using yarns having differing elasticity values. For example, the bands 1042, 1044 can be formed by knitting primarily with one of the yarns where the other(s) are just carried across to the next section where the roles are reversed.

As shown, the head strap 1040 can be formed into a tubular shape that defines a lumen 1046. The tubular shape of the head strap 1040 can incorporate a series of the bands 1042, 1044. As described directly above, the bands 1042, 1044 can have differing elasticity. In some configurations, the bands 1042, 1044 can have alternating elasticity. Such a configuration can allow a series of beads 1050 or the like to be inserted into the lumen 1046 defined by the tubular shaped sleeve of the head strap 1040. In some configurations, the beads 1050 and the tubular shape of the head strap 1040 can be integrated into a single component (i.e., the two can form a single component as shown in FIG. 11). In some configurations, the beads 1050 and the tubular shape of the head strap 1040 can be separate components. The beads 1050 can be advanced or retracted to alter a length or circumference of the strap or headgear component, for example, but without limitation. As such, the varied stretch properties in the bands 1042, 1044 can be used to adjust the length of the string of beads 1050 that can be pulled through the tubular sleeve of the head strap 1040, which can be formed by braiding, for example but without limitation. The relatively more stretchy bands 1042 can expand to accommodate the beads 1050 while the relatively less stretchy bands 1044 can resist circumferential expansion and can act to hold the beads 1050 in position.

The illustrated configurations can provide increased reliability and improved ease of manufacture. Accordingly, such configurations can result in less rejects and less returns.

Multi-Yarn Knit in a Continuous Braid Employing Thermoplastic Yarn

With reference now to FIGS. 12 and 13, a combination of technologies can be used to modify the braid or the weave. In some configurations, such as those shown in FIG. 12, a thermoplastic material can be used in the braided or woven strap 1060. The thermoplastic material allows deformation under heat, which allows welding, such as ultrasonic welding, calendaring, fusing, and the like. For example, additional parts can be welded on to help create at least a portion of, if not a complete, headgear assembly. In the illustrated configurations, a clip, buckle, or other mechanical components 1062 can be secured to the strap 1060 using welding, such as ultrasonic welding, for example, but without limitation.

In some configurations, the thermoplastic nature can be used to change properties of the strap 1060 in specific regions (e.g., alter the elasticity). For example, in the illustrated configuration, a portion 1064 of the strap 1060 is shown crushed and fused, which can alter characteristics in that region of the strap 1060. In some configurations, such as that shown in FIG. 13, calendaring can be used, for example but without limitation, to add a pattern 1066. In some configurations, the strap 1060 can be branded by taking advantage of the thermoplastic characteristics.

Thus, in configurations employing thermoplastic yarn, the thermoplastic yarn can allow permanent thermoplastic, post-knitting, deformation, for example but without limitation. An advantage of such a construction is that the thermoplastic yarn can help incorporate features that would be otherwise impossible, difficult, and/or expensive to provide.

Multi-Yarn Knit in a Continuous Braid Employing a Fancy Knitting Pattern

With reference to FIGS. 14, 15*a*, 15*b*, and 16, configurations are illustrated in which a strap 1070 can feature a knit that is varied to create features and properties. In some configurations, tactile properties can be created or altered by adjusting or varying the knit. In some configurations, features can be created during the knitting process simply by using different knitting patterns.

As illustrated, the knitting machine can be adjusted to create a braid or a knit that incorporates desired features. For example but without limitation, in some configurations, such as that shown in FIG. 14, multiple loops can be created for tactile and/or functional reasons. In the illustrated configurations, the loops can be used in conjunction with hook-style fasteners or the like. For example, in FIG. 14, the loops can provide a differing tactile feel while also providing a loop segment 1072 that can improve connection with hooks of a hook-and-loop style fastener. In some configurations, such as those shown in FIGS. 15*a* and 15*b*, for example, well defined loops 1074 can be used as catches for hooks on a connector member 1076. In other words, rather than having to attach separate catches for the hook of a clip, the well-defined loops 1074 can be used to secure the hook of the clip 1076. In some configurations, such as shown in FIG. 16, for example, holes 1080 can be formed that can be used to receive buttons or posts, for example but without limitation.

An advantage of such a construction is that all of the different properties are still part of the same knit with all of the advantages of knitting. In other words, there is only one manufacturing process to create the strap and no or minimal waste is created.

Multi-Yarn Knit in a Continuous Braid Incorporating Tactile Elements

Figure 17:
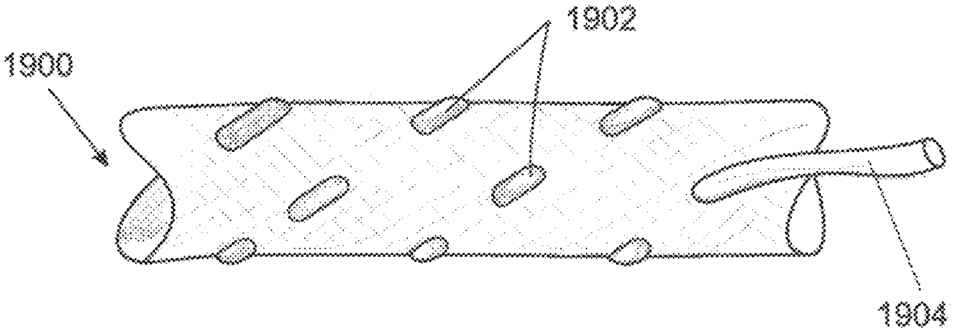
FIGS. 17-19 are views of straps having friction pads.
Figure 18:
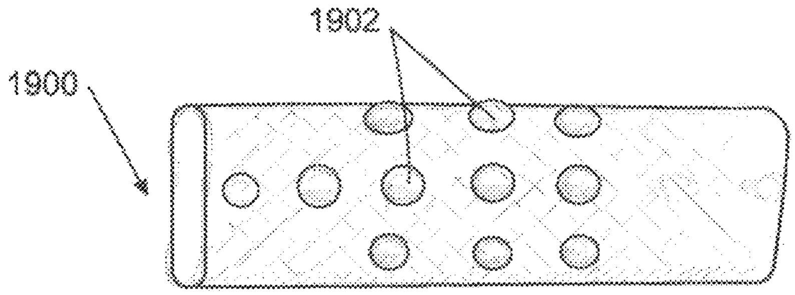
Figure 19:
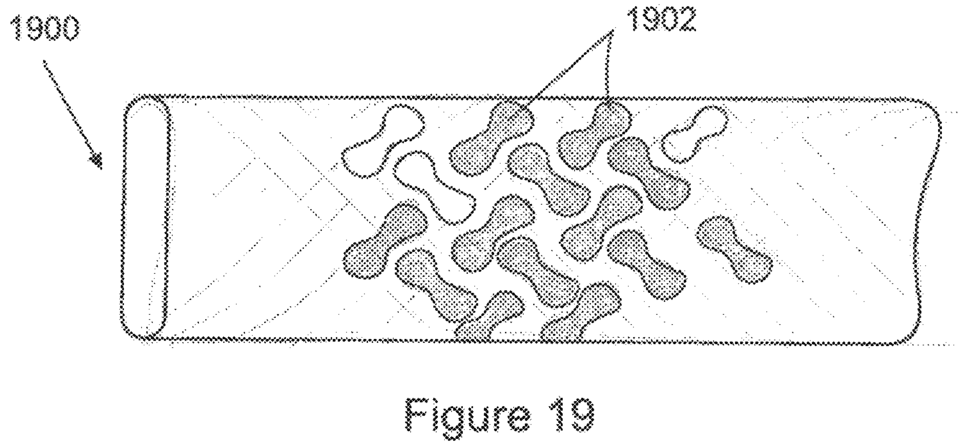

With reference FIGS. 17-19, a strap or headgear component 1900 is illustrated that has incorporated a surface texture 1902. The surface texture can be used to increase grip, for example but without limitation.

As illustrated, in some configurations, such as that shown in FIG. 17, the knit or braid can incorporate a string 1904, such as a rubber string, a silicone string, or the like. Such configurations can use exposed regions of the string 1904 to create the surface texture, which defines a high friction component, such as a pad, that can be integrated into the braid of the strap or headgear component 1900.

In addition to, or as an alternative to, using the multi yarn knit to create a textured surface 1902, other techniques also can be used. For example, in some configurations, such as those shown in FIGS. 18 and 19, screen printing can be used to create a textured surface 1902. Screen printing has the additional advantage of complete freedom in shape and size of the print. In the illustrated configurations, rubber dots can be screen printed. In some configurations, other shapes can be defined. In some configurations, other shapes can be defined by screen printing or the like. For example but without limitation, the shapes can change as desired and, in some instances, depending upon fashion desires.

In some configurations, being able to provide surface texture can facilitate better control over how certain portions of the headgear behaves or feels when disposed against the skin, for example.

Continuous Braids with Varied Shapes

With reference now to FIGS. 20-32, various configurations are shown in which headgear and head straps can be created having varied shapes, which can be desired for multiple reasons.

Figure 20:
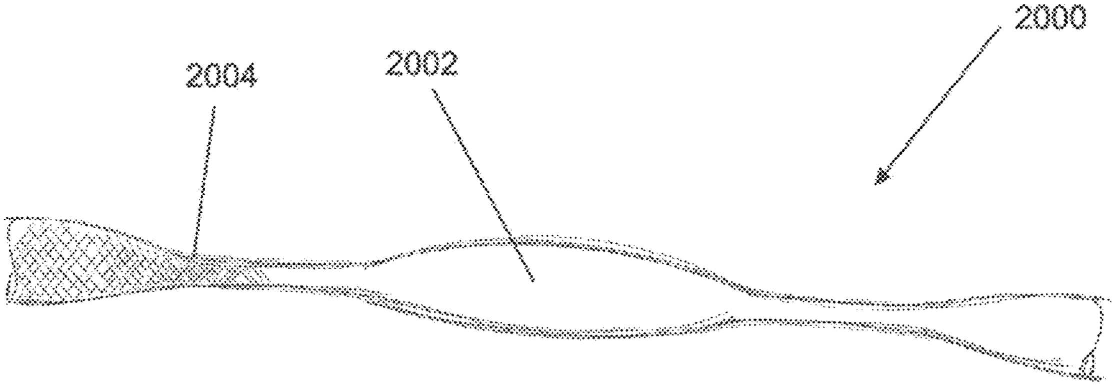
FIGS. 20 and 21 are views of a strap having a non-uniform width along the length.
Figure 21:
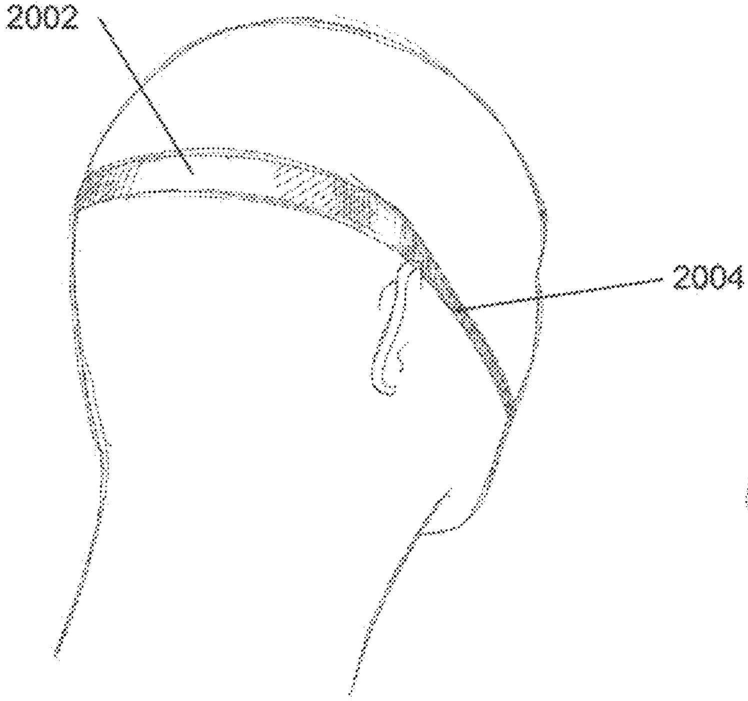
Figure 23:
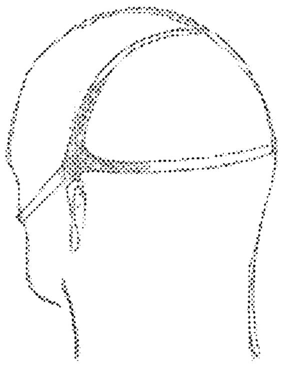
FIGS. 22 and 23 are views of a strap having a more complicated shape.

With reference first to FIGS. 20 and 21, the illustrated configurations generally involve straps 2000 having varied cross sections. In the illustrated configurations, the headgear can be created as a continuous knitting process as described above. As illustrated, the knit can have wider regions 2002 and narrower regions 2004 and can be cut for finishing with appropriate or desired hooks, buckles, clips or the like. Such configurations can improve the fit, form and function of the headgear strap.

Figure 22:
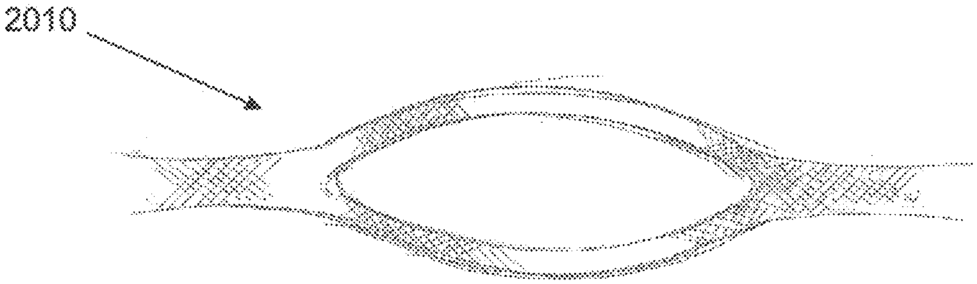
Figure 24:
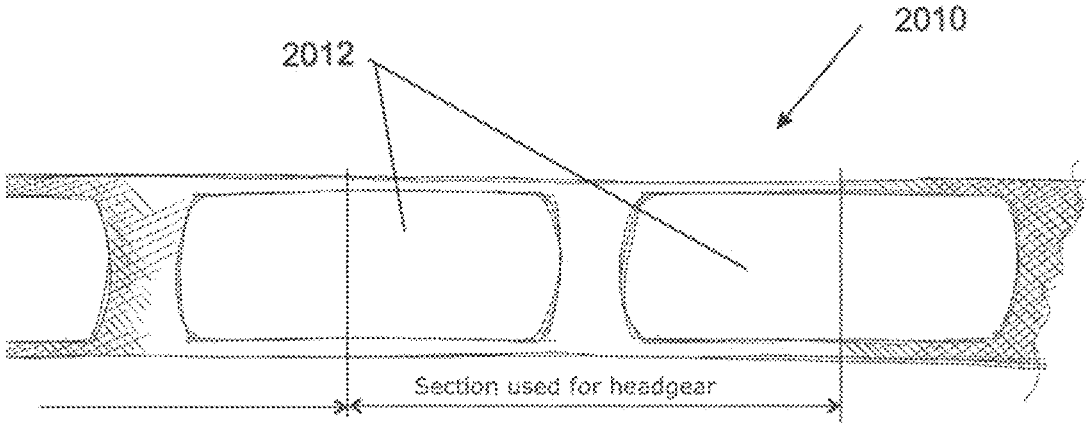
FIGS. 24-26 illustrate headgear strap formed as a continuous member.
Figure 25:
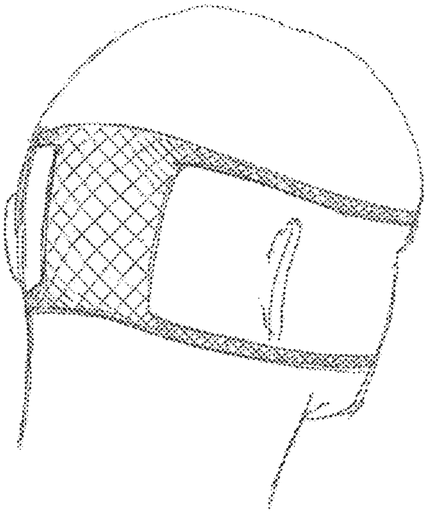
Figure 26:
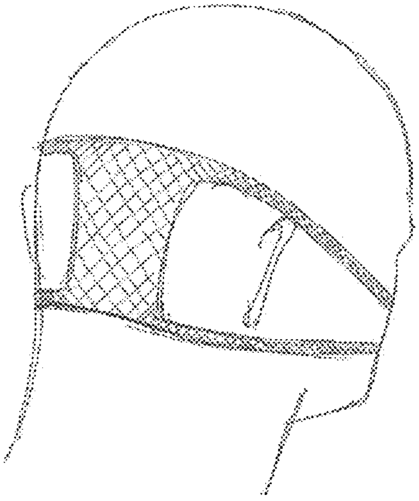

With reference to FIG. 22—, these configurations generally involve straps 2010 that are a more complex knit with splits and joins. In some configurations, the knit, much like that of FIGS. 20 and 21, can be formed as an endless strip that can be cut later into individual straps or headgear assemblies. In the illustrated configurations, the straps 2010 can define windows, openings or other large voids 2012 (see FIGS. 22-23, for example)_that are included within the materials of the braid and/or knit. In some configurations, the straps can be configured such that two different varieties of headgear can be formed from the same braid and/or weave (see FIGS. 27-29, for example). For example, in some configurations, a window can be formed within the braid and/or weave that can be positioned on a back of a user's head (see FIG. 29) while, if split, the portions of the strap 2010 that form the window 2012 can be used as a forked headgear with two strap ends that connect to an interface or the like (see FIG. 28). The two strap ends can receive any suitable connector, buckle, hook, clip or the like.

Figure 27:
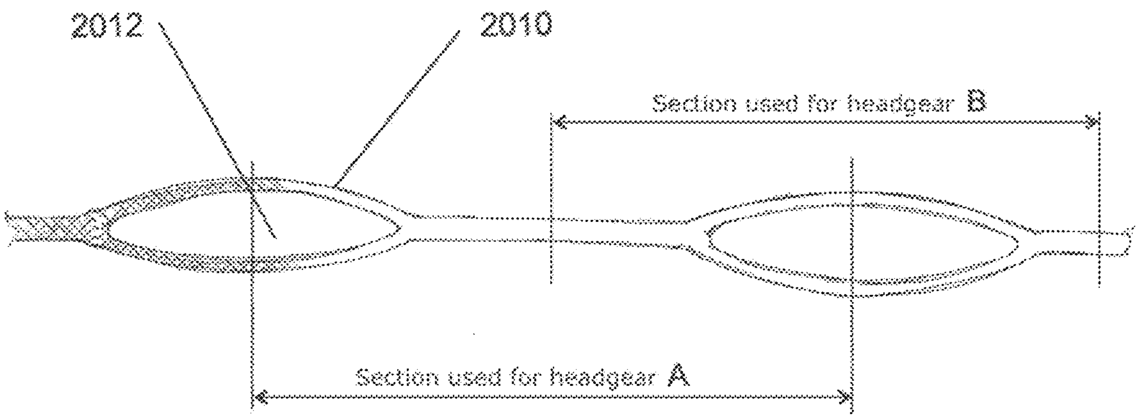
FIGS. 27-29 illustrate two headgear straps formed as a continuous member.
Figure 28:
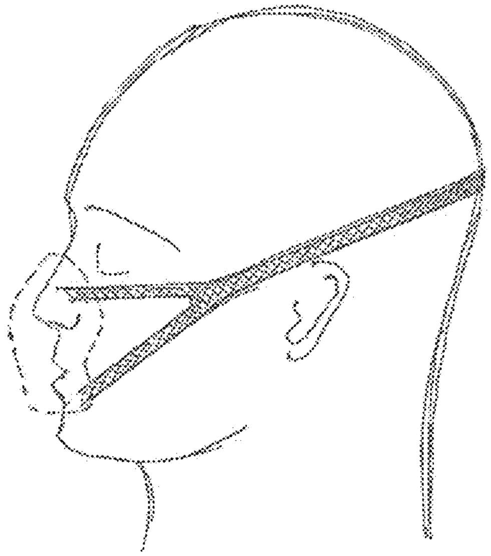
Figure 29:
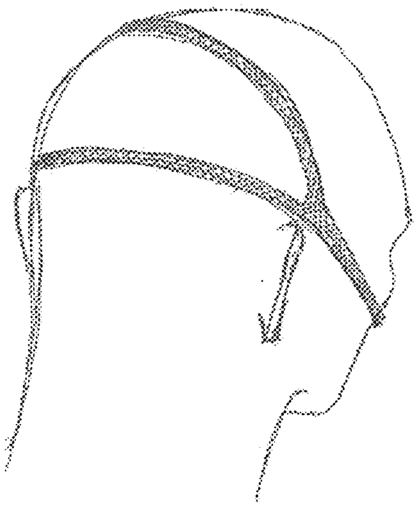
Figure 30:
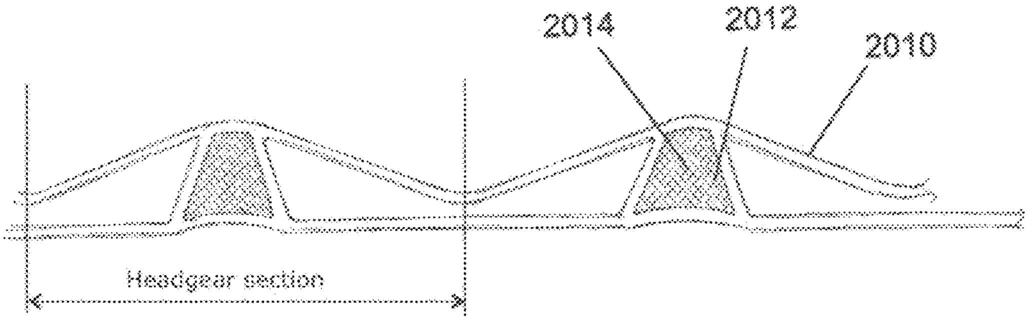
FIGS. 30-32 illustrate a headgear strap formed from a continuous member.
Figure 31:
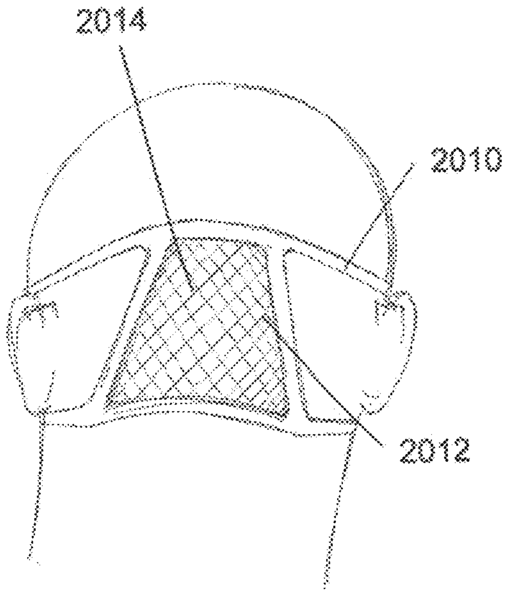
Figure 32:
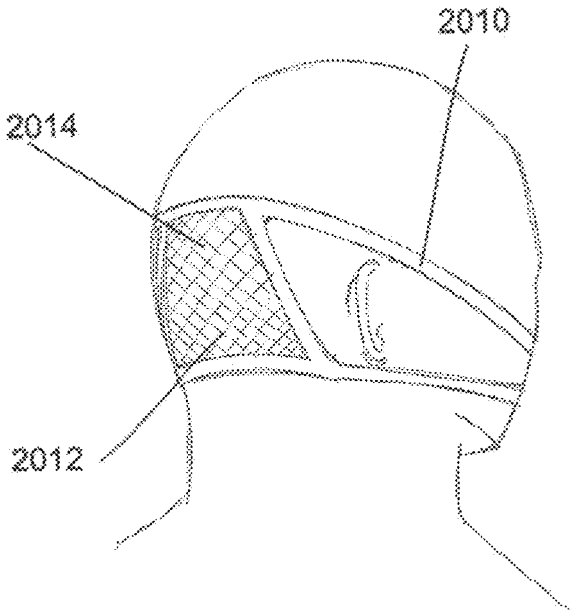
Figure 33:
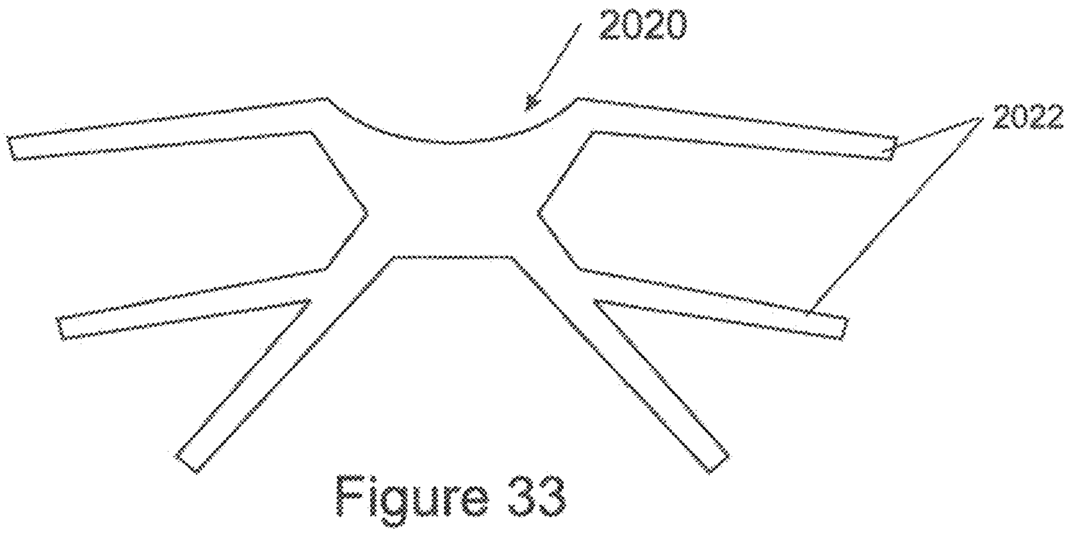
FIGS. 33-36 illustrate headgear formed as a single knit.

With reference now to FIGS. 30-32, a further configuration is illustrated that is similar in some respects to the configuration of FIGS. 27-29. In the configurations of FIGS. 30-32, the windows 2012 discussed above can include a filling component 2014. In some configurations, the windows 2012 can include a mesh material 2014. In some configurations, the mesh material 2014 can be integrally formed with the straps 2010 that generally define the windows 2012. In some configurations, the mesh material 2014 can be formed separately and secured into the windows 2012 or onto the straps 2010 in any suitable manner. In some configurations, the headgear can be formed as a continuous strip that can be severed into multiple headgear during manufacturing.

Single Knit Headgear

With reference now to FIGS. 33-36, an entire, complex, headgear 2020 can be knit in one seamless knit. In some configurations, two or more of the straps 2022 used in the headgear 2020 can be integrated into a single knit. In some configurations, a majority of the straps 2022 used in the headgear 2020 can be integrated into a single knit. In some configurations, all of the straps 2022 used in the headgear 2020 can be integrated into a single knit.

Figure 34:
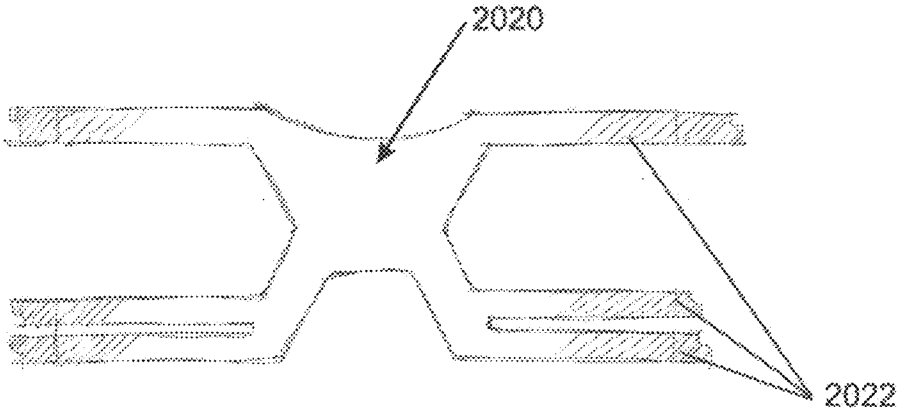
Figure 35:
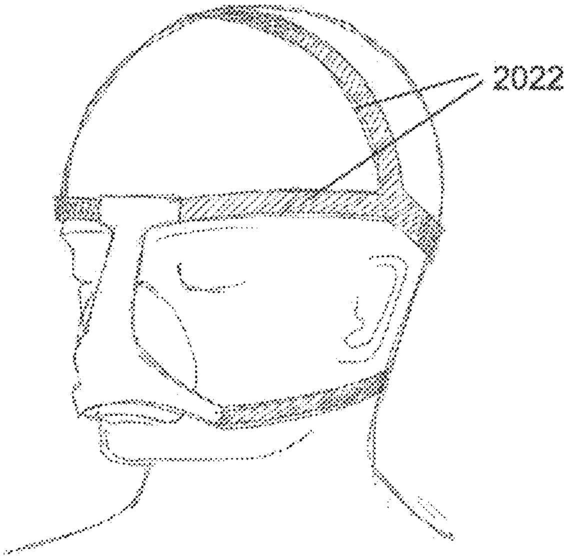
Figure 36:
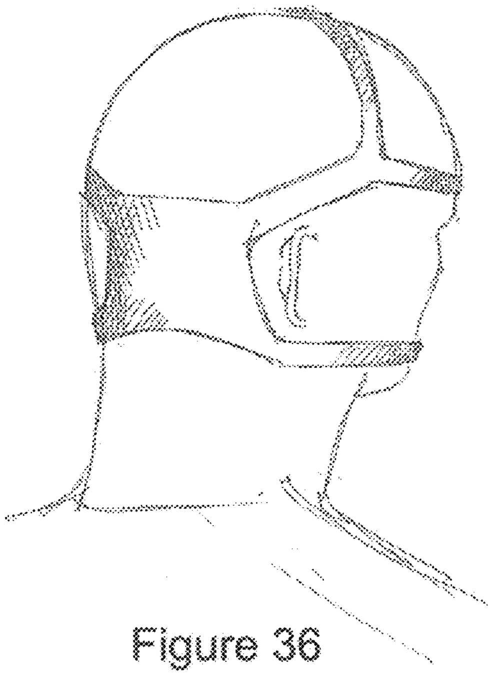
Figure 45:
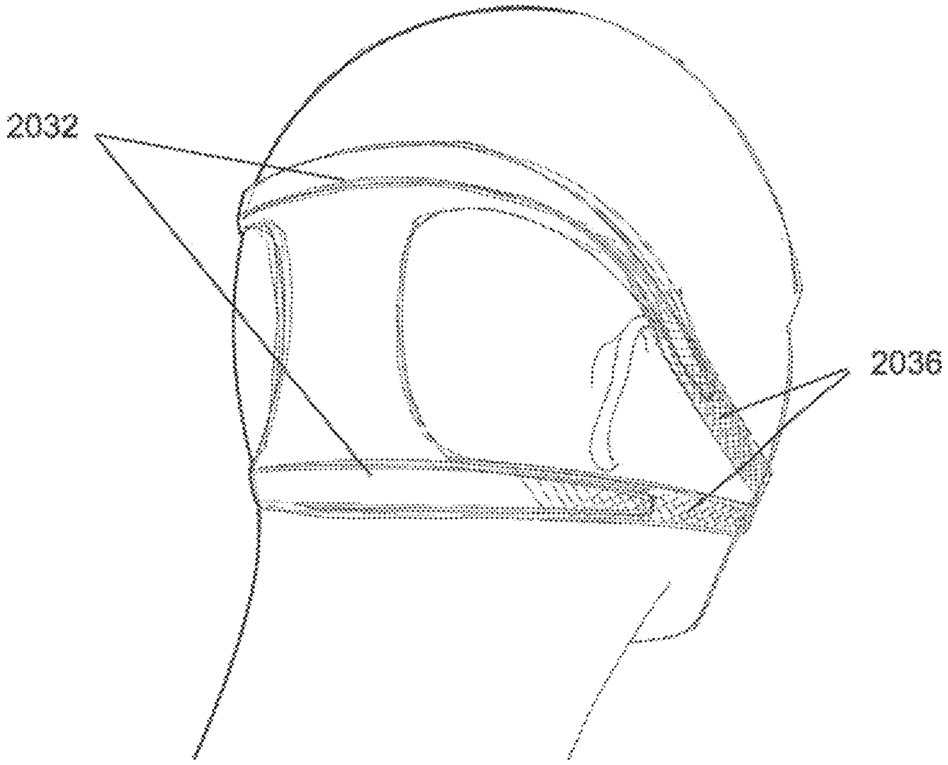
Figure 46:
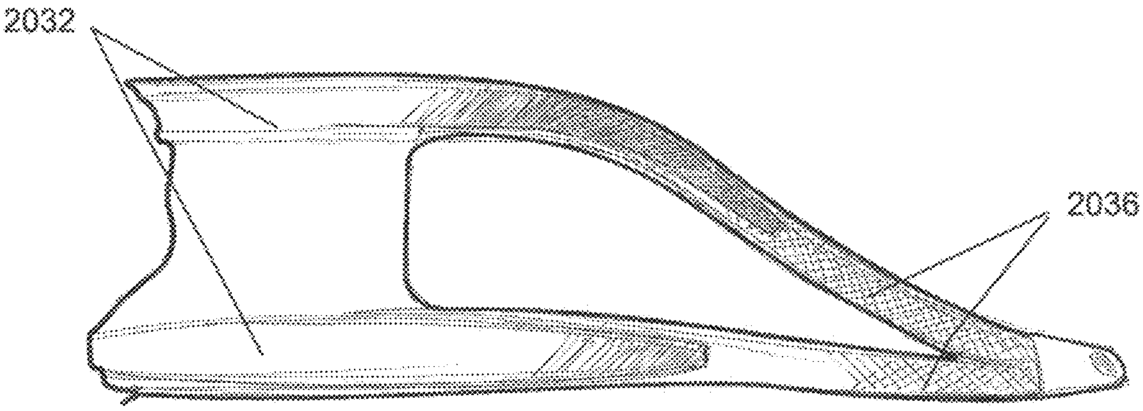

In some configurations, each headgear 2020 can be knit individually. By forming the entire or the majority of the headgear 2020 in a single knit component, very complex shapes can be obtained without undertaking labor intensive stitching or welding steps. Generally, such a seamless knit configuration is less likely to be continuous (i.e., not an endless string of headgear assemblies). In some configurations, however, the seamless knitting process can be used to form headgear 2020 having a rather complex configurations (e.g., three separate strap components 2022 on each side of the headgear) while still be formed in a continuous strip of headgear assemblies, as shown in FIG. 34.

Headgear Incorporating Rigid or Semi-Rigid Inserts

With reference now to FIGS. 37-46, headgear 2030 can be created that includes one or more receiving regions, such as pockets, recesses or voids that receive and/or enclose rigid or semi-rigid inserts 2032 to help define a resting shape of the headgear 2030. One or more of the inserts 2032 can be removable from the pockets, recesses or voids. For example, the inserts 2032 can be removed for cleaning of the headgear 2030. In some situations, the headgear 2030 can be used without the inserts 2032. In some situations, the inserts 2032 can have different characteristics and can be interchanged to vary one or more characteristic of the associated headgear 2030. Moreover, in some situations, the inserts 2032 can be moved to different regions of the headgear 2030. For example, the inserts 2032 can be moved among a set of receiving regions to alter one or more characteristic of the headgear 2030.

One of the difficulties sometimes encountered with more complex headgear is getting the straps into the correct location when donning the headgear. In other words, many of the current headgear configurations on the market function well when in use. However, when not in use, the numerous straps can easily become tangled and knotted, which frustrates users each time they have to put the mask back on. By utilizing straps having pre-defined resting shapes, headgear tangling can be reduced or eliminated while also creating a shape that will aid the user in understanding how best to approach wearing the headgear on their first trial.

As used herein, the rigid or semi-rigid structure 2032 can be positioned internally or externally. In some configurations, the rigid or semi-rigid structures 2032 can be positioned within the hollow defined by the strap (e.g., defined by the braid). The rigid or semi-rigid structures 2032 can be secured in position using any suitable techniques. In some configurations, the rigid or semi-rigid structures 2032 can be secured with adhesive, with stitching or with any other technique. In some configurations, the rigid or semi-rigid structures 2032 can maintain a specific shape of the head gear when in the resting position. In some configurations, the rigid or semi-rigid components 2032 can be applied to a single strap or multiple strap head gear arrangements.

As used herein, the resting shape is a shape that reduces or eliminates the likelihood of entanglement of the headgear when the headgear is not in use. The resting shape has an added benefit of also making it more obvious how the head gear should be put on by the user.

The rigid or semi-rigid member 2032 can be positioned in or on any one or more of the components of the headgear. In some configurations employing multiple rigid or semi-rigid members, the multiple members 2032 can be completely separate of each other. In some configurations employing multiple rigid or semi-rigid members 2032, the multiple members 2032 can be interconnected in any suitable manner.

In some configurations, as shown in FIGS. 39 and 40, for example, a crown strap 2034 of the headgear assembly can include two different rigid or semi-rigid members 2032 that are positioned within a stretchable strap 2036. The strap can be stretched during donning but returns to a contracted position following doffing. In some configurations, the stretching occurs in regions separating the two or more rigid or semi-rigid members 2032. An example of stretching of a strap 2036 in regions that do not including the rigid or semi-rigid member 2032 is shown in FIGS. **38*a*-38*c*. In some configurations, the stretching occurs in the regions generally enveloping the rigid or semi-rigid members 2032**.

In some configurations, such as those shown in FIGS. 41-44, the rigid or semi-rigid member 2032 can have a more complex shape that connects the single rigid or semi-rigid member 2032 with two or more strap members 2036. In some such configurations, the rigid or semi-rigid member 2032 can help define a shape of the headgear 2030 by holding two or more straps 2036 in a desired position relative to each other. For example, in some configurations, the rigid or semi-rigid member 2032 can be a complex spreader that holds two or straps 2036 spread apart in a desired angular orientation. In some configurations, such as that shown in FIGS. 45 and 46, the rigid or semi-rigid member 2032 can provide support to a base and back portion of the headgear assembly 2030. The rigid or semi-rigid members 2032 can span the rear portion of the user's head and can wrap forward such that the straps 2036 are presented forward to simplify donning the headgear. Other configurations are possible.

Strap Incorporating Internal Stretch Increasing Elements

Figure 47:
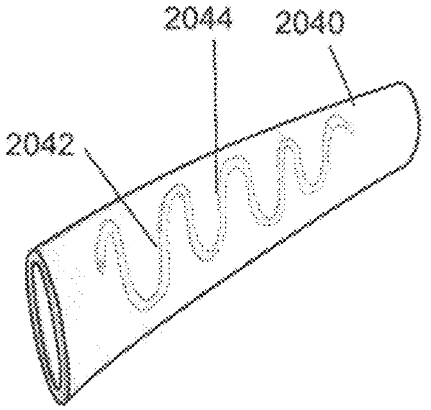
FIGS. 47-56 illustrate straps with length adjusting segments.
Figure 48:
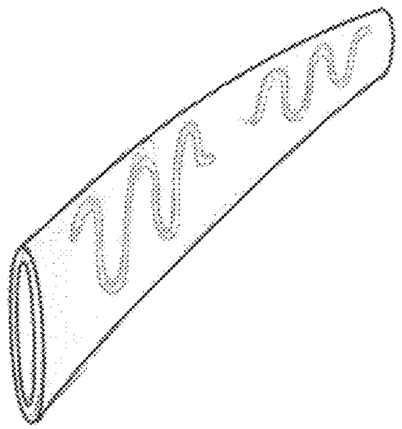

With reference now FIG. 47-56, certain configurations of straps 2040 can include an internal structure 2042 that has multiple segments 2044. In some configurations, such as shown in FIGS. 47 and 48, the internal structure 2042 can be wound or looped. In some configurations, the material for the internal structure 2042 can be non-stretch thread (e.g., natural fiber thread (e.g., cotton or wool) or synthetic thread), a low-stretch elastic member or the like. In some configurations, the internal structure 2042 can extend throughout the strap. In some configurations, the internal structure 2042 can be limited to specific regions in which adjustability might be desired.

Figure 52:
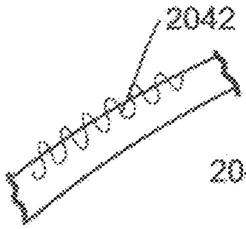
Figure 53:
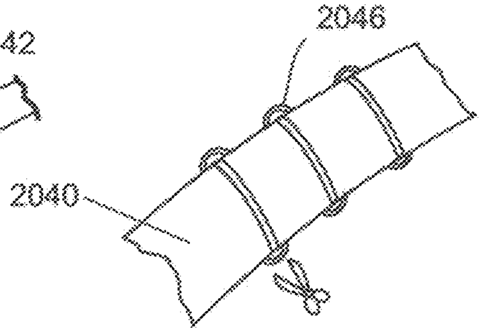
Figure 54:
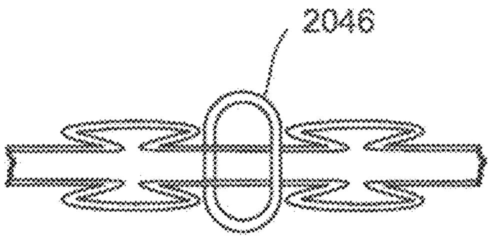
Figure 55:
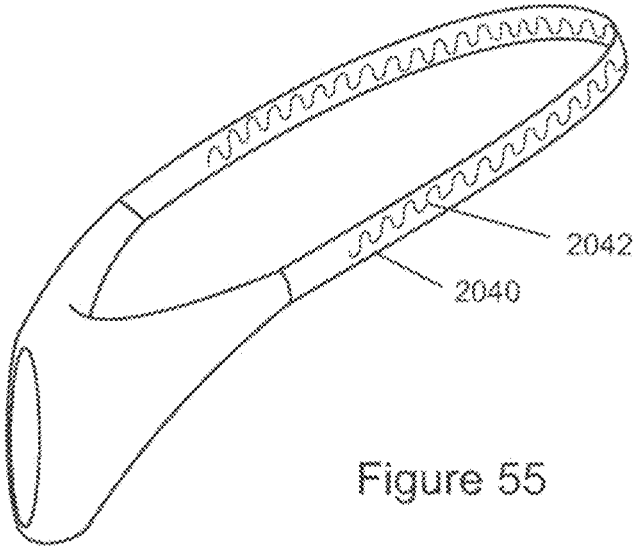
Figure 56:
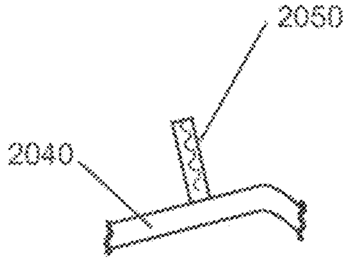
Figure 57:
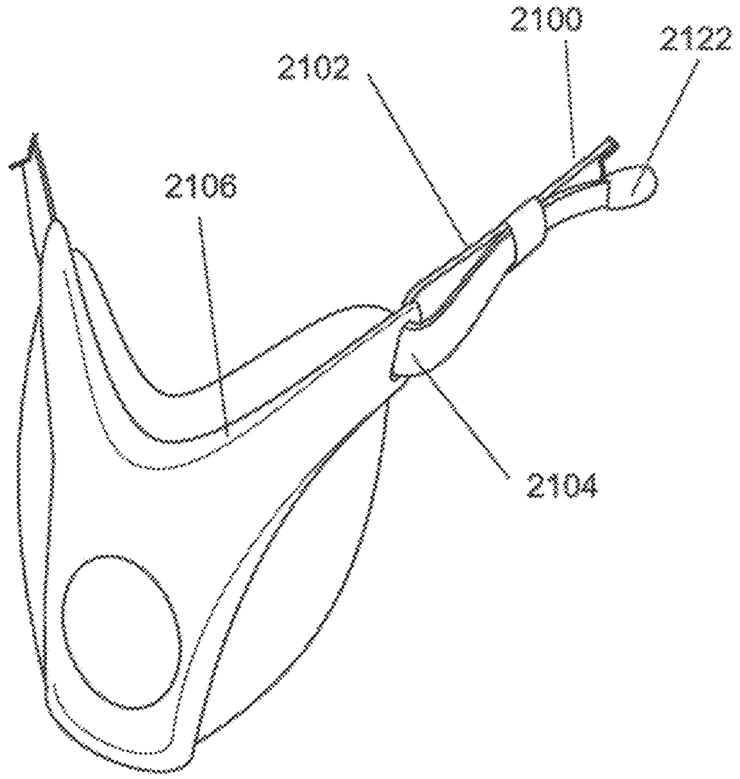
FIGS. 57-62*c* illustrate headgear incorporating a tie-down and strap management system.
Figure 58A:
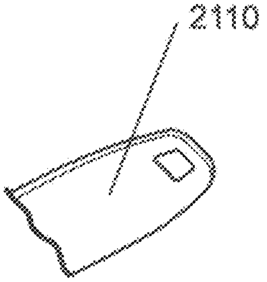
Figure 58B:
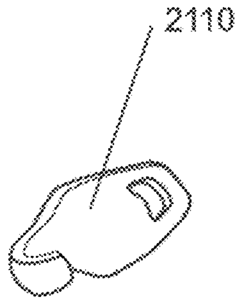
Figure 59A:
Figure 59B:
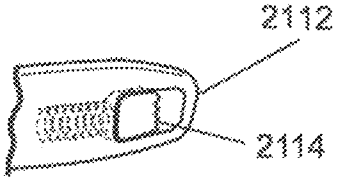
Figure 60A:
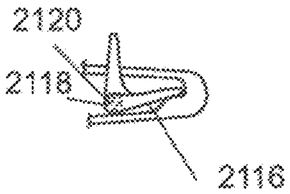
Figure 60B:
Figure 60C:
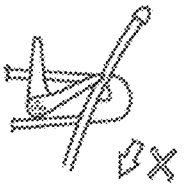
Figure 60D:
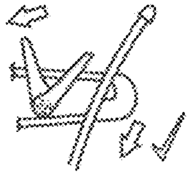
Figure 61A:
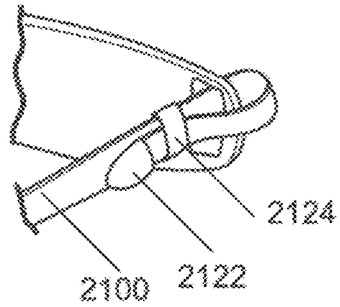
Figure 61B:
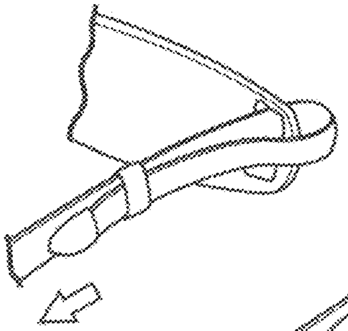
Figure 61C:
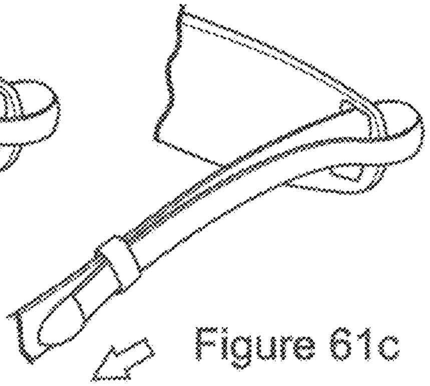

In some configurations, the structure 2042 can be fully internal. In some configurations, such as shown in FIG. 52, at least a portion of the structure 2042 can be raised to allow severing of the strap in locations underlying the raised structure portions 2042. In some configurations, such as shown in FIGS. 53 and 54, the strap 2040 can include loops 2046 that restrain folded material until the loops 2046 are broken or cut, for example but without limitation. As shown in FIG. 56, a folded region 2050 or the like can be provided with an extensible portion of the structure 2042 housed within the region 2050. When the region 2050 is separated from the portions of the strap 2040 to either side, the structure 2042 connects the portions of the strap 2040 while facilitating expansion of the strap 2040. Separation can occur through cutting or axial forces applied along the length of the strap or within the segment of the strap where elongation is desired.

The segments 2044 can be connected or connectable together. The segments 2044 resist stretching of the straps 2040. Accordingly, in some configurations, at least a portion of each of the multiple segments 2044 can be secured to at least a portion of the strap 2040 in some suitable manner. When two adjacent segments 2044 are separated, the strap 2040 can be stretched in locations between the segments 2044. In some configurations, when the two adjacent segments 2044 are separated, the strap 2040 can be stretched between the location points on the strap 2040 at which the strap 2040 is secured to the segments 2044.

Figure 49:
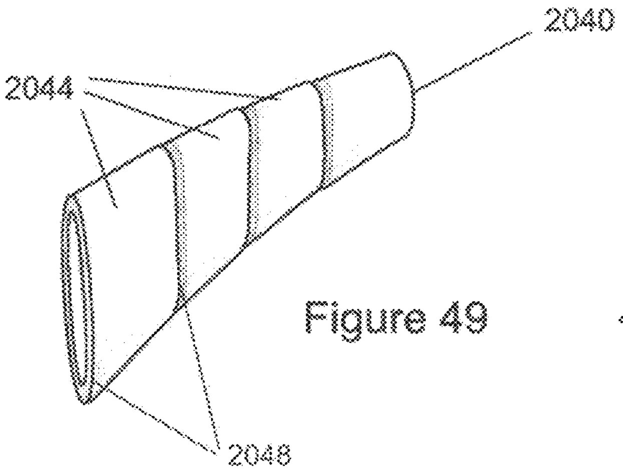
Figure 50:
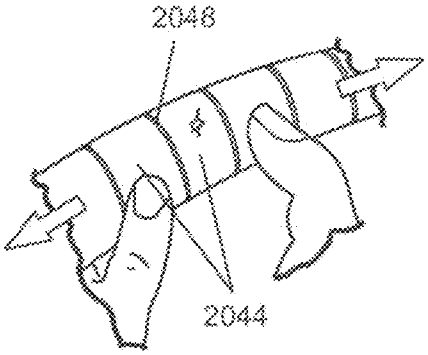
Figure 51:
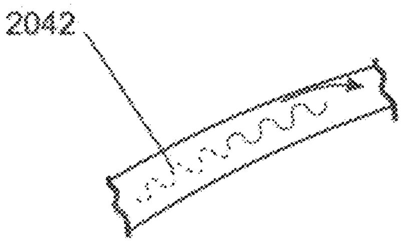

In some configurations, such as shown in FIGS. 49-50, the internal structure 2042 can be snapped or broken into segments 2044 in order to increase the stretch of the strap 2040. In some configurations, the internal structure 2042 can be stitched into the head strap 2040 and thereby limit the initial amount of stretch available. The internal structure 2042 can include a series of sections 2044 that, when pulled with a predetermined force or bent with a predetermined force or some combination of the two, will separate at a snap point 2048, for example but without limitation. In some configurations, the snap points 2048 will snap and permanently add a small amount of stretch to the head strap 2040. By providing multiple snap points 2048 across several sections of the head strap 2040, the strap can dramatically increase elasticity. While the illustrated configurations illustrate single straps 2040, the same structure also can be used in multiple strap headgear.

To assist with locating the snap points, visual snap point indicator can be used. The indicators can be graphical representations. The graphical representations can indicate to the user the areas of the head gear that are appropriate to snap It is believed that users prefer the simplicity of not only having a single strap head gear but also not having numerous tabs that need to be adjusted time and time again for a desired fit. This poses a challenge in how to create one single strap that fits the large variation between head circumferences of the smallest and biggest size of users. By incorporating an 'invisible' adjustment such as those described above, a greater number of users can be accommodated in a way that adds little or no additional structure, tabs or buckles.

Headgear Incorporating a Tie Down and Strap Management System

With reference now to FIGS. **57-62*b*, a single strap head gear 2100 is shown with a tie down and strap management system 2102** that is arranged and configured in accordance with certain features, aspects and advantages of the present invention.

As used herein, a tie down 2102 can be a strap management system that allows a single strap head gear 2100 to be folded back onto itself via a loop point, buckle or the like 2104. As illustrated, the strap 2100 can be folded back at a component that is integrated into the interface or mask assembly 2106 or the strap 2100 can be folded back at a component that is separate from or separable from the interface or mask assembly 2106, such as a hook, clip, connector or the like (see FIG. **58*b***, for example).

The strap 2100 can then be locked at a specific point providing less or more length via a buckle (e.g., FIG. **58*a*, 58*b* or 59*a*) or spring loaded mechanism (e.g., FIG. 59*b*, and FIGS. 60*a*-60*d*). In the illustrated configurations, the buckle 2110 and/or the spring loaded mechanism 2112 can be provided with serrations, teeth or the like 2114 (see FIG. 59*b*) to provide added grip on the strap 2100. In some configurations, as shown in FIGS. 60*a*-60*d*, a lever 2116 can be used to secure the strap 2100 in position. In some configurations, the lever 2116 can be biased by a spring member 2118. In some configurations, the lever 2116 can have a resilient configuration such that no spring member is required and the lever 2116 is simply a cantilevered member. In some configurations, the lever 2116 rotates about a shaft 2120. In some configurations, the mechanism resists movement of the strap 2100 in a first direction but generally allows movement of the strap 2100** in a second opposite direction.

As used herein, a loop point is a point at which the head strap 2100 can be folded back on itself. This can be built into the mask, into the seal or and through an additional buckle or the like.

As used herein, a grip point 2122 is a rigid and/or semi-rigid material that is placed on the strap 2100 to facilitate gripping during adjustment of the strap 2100.

Figure 62A:
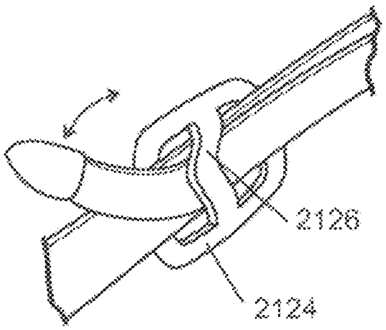
Figure 62B:
Figure 62C:
Figure 63:
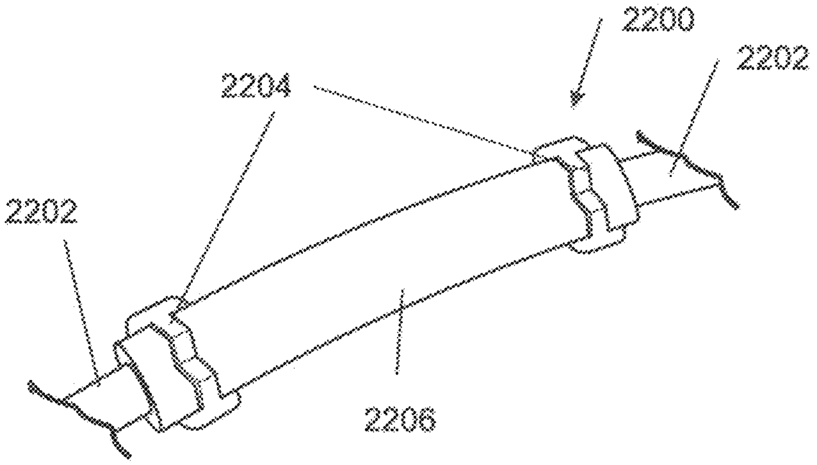
FIGS. 63-69 illustrate headgear incorporating a stretch limiting system.

As illustrated in FIGS. **61*a*-61*c*, the length of the strap 2100 that is positioned between a slider 2124 and the loop point can be adjustable. The slider 2124 can move along the strap 2100. In the illustrated configuration, the slider 2124 can be in contact with two overlapping segments of the strap 2100. The slider 2124 can have any suitable configuration. As shown in FIGS. 62*a*-62*c*, the illustrated slider 2124 has a central member 2126 that depresses a portion of the strap 2100 and effectively locks the slider 2124 in position along the strap 2100**.

By utilizing a tie down system, users are free to tweak their initial set up as and when desired at any future date. Accordingly, if the users face shape changes or the elasticity of the strap weakens over years of use, there is still a suitable adjustment method to account for this.

Headgear Incorporating Stretch Limiting System

With reference now to FIGS. 63-69, a strap 2200 is illustrated that can incorporate an elastic head strap 2202 that uses buckles 2204. In the illustrated configurations, two or more buckles 2204 and a relatively non-stretch component 2206 can be used to adjust the degree of stretch that can be provided along a length of a strap 2200.

Figure 64:
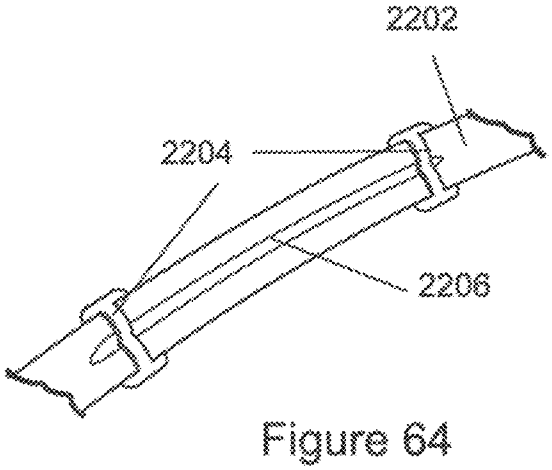

In some configurations, such as illustrated in FIG. 64, the non-stretch component 2206 can be a relatively (relative to the strap) non-stretch sleeve. The non-stretch sleeve has a length that is less than the stretch component (e.g., elastic strap). As used herein, a non-stretch sleeve can be either an external sleeve (FIG. 63) or an internal structure that has non-stretch properties (FIG. 64) and that is used in conjunction with a stretchable head strap 2202.

Figure 67A:
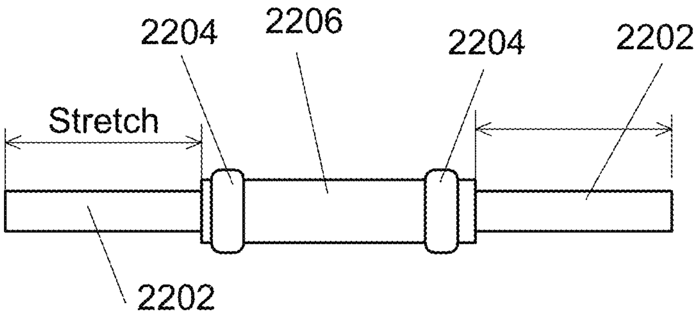
Figure 67B:
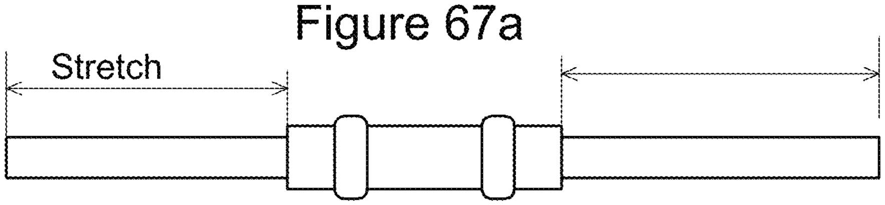
Figure 68:
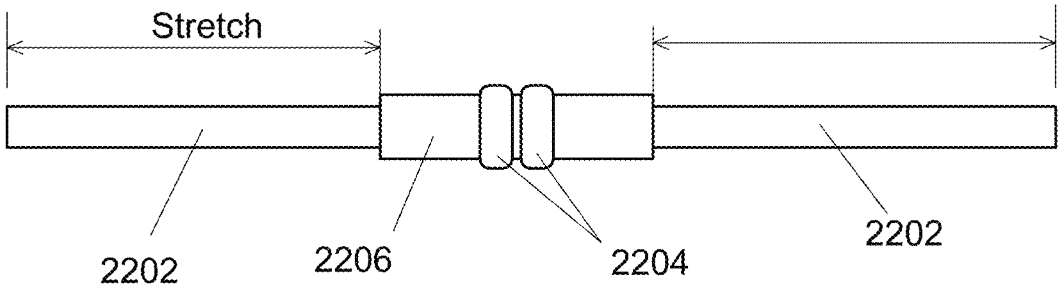

In the illustrated configurations, one or more buckles, clips or the like 2204 can be used to increase or decrease the ability of the strap 2202 to stretch. In some configurations, two small buckles 2204 can be used to limit the amount of elastic deformation of the strap 2202 available to the user. Such configurations allow the users to quickly and easily fine tune the forces that they experience when using the headgear 2200. In other words, the user is able to use the buckles, clips or the like 2204, to couple the relatively more stretchable portion to the relatively less stretchable portion in various locations. This allows the relatively less stretchable portion to resist stretching of the relatively more stretchable portion between the two buckles, clips or the like 2204. In other words, as shown in FIGS. 67*a*-67*c*, moving together two clips 2204 that lock or otherwise secure together the relatively less stretchable component and the relatively more stretchable component will increase the length of relatively more stretchable strap 2202 available for stretching, which can increase the overall amount of stretch available to the user.

Figure 65A:
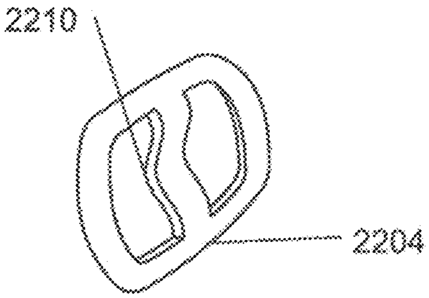
Figure 65B:
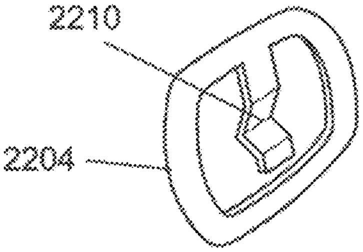
Figure 66A:
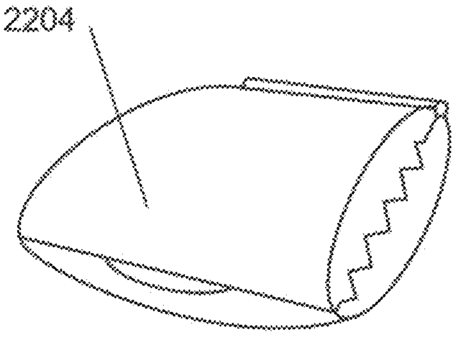
Figure 66B:
Figure 69:
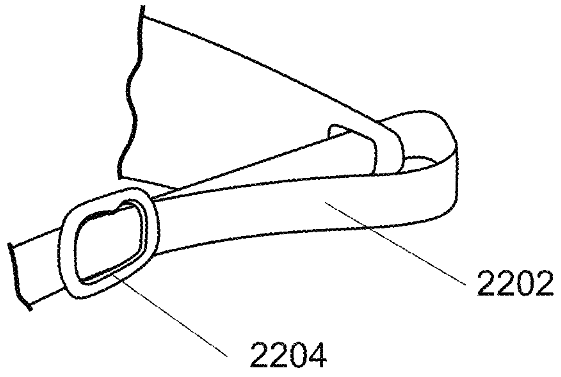
Figure 70:
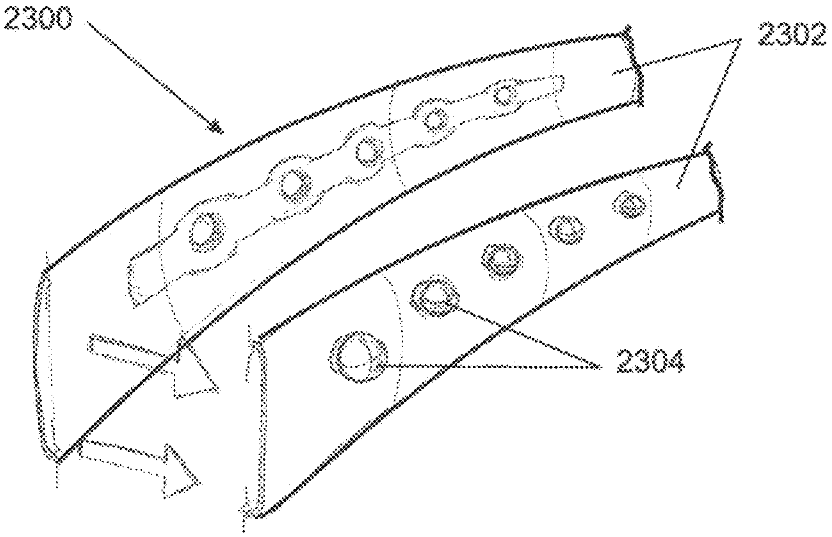
FIGS. 70-76 illustrate headgear incorporating a stretch limiting system using push-buttons or domes.

The buckles and clips can have any suitable configuration. In some configurations, the clips 2204 can be generally clam-shell in configuration. In some such configurations, such as shown in FIGS. 66*a* and 66*b*, the clips 2204 can fold closed and lock in a closed position. In some such configurations, the clips 2204 can include serrations or the like 2208 to define teeth or the like to help secure the clips 2204 in position and to help hold the relatively non-stretch component to the relatively stretch component. In some configurations, the clip 2204 can include a member that slides along a slot defined within the relatively non-stretch component 2206. In some configurations, such as shown in FIGS. 65*a* and 65*b*, the clip 2204 can include a protruding component 2210 that extends inwardly through the slot and engages against the relatively stretchable component 2202 to lock the relatively non-stretch component 2206 and the stretch component 2202 together. In some configurations, such as that shown in FIG. 65*a*, the protruding component 2210 extends fully across an opening defined by the clip 2204. In some configurations, such as that shown in FIG. 65*b*, the protruding component 2210 extends only partially across the opening such that the clip 2204 can be installed onto a strap 2202 without having access to any end of the strap 2202. In some configurations and as shown in FIG. 69, the illustrated configurations can be used in a tie-down arrangement or in conjunction with a tie-down arrangement such as those described above.

Headgear Incorporating Stretch Limiting System Using Push-Buttons/Domes

With reference now to FIGS. 70-76, a stretch limiting system 2300 is illustrated that incorporates an elastic head strap using limiters, such as push buttons, domes or the like, to limit stretch of the strap.

In the illustrated configurations, a generally non-stretch sleeve 2302 can be used to limit the stretch of the relatively more stretchable strap. The sleeve 2302 can be an external sleeve or an internal structure that can be used in conjunction with a relatively stretchable head strap. In some configurations, the sleeve 2302 can be an external sleeve that is formed in two or more separable pieces, such as that shown in FIG. 70. In some configurations, the sleeve 2302 can be formed of two or more separable pieces that can snapped or clipped together, such as that shown in FIG. 70, for example.

Figure 71:
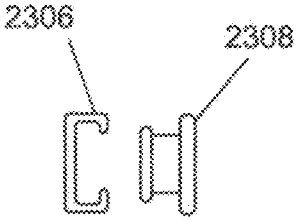

In some configurations, push buttons, domes or the like 2304 can be positioned at predetermined spacing along the non-stretch sleeve 2302. An example of a configuration of a push button 2304 is shown in FIG. 71. As illustrated, there is a base portion 2306 and a head portion 2308. The base portion 2306 has a flange and the head portion 2308 has a flange. When engaged, the flanges interlock the base portion 2306 and the head portion 2308 together. Locking these buttons in specified patterns can increase or decrease the stretching capabilities of the strap and therefore create varying sizes for each user.

Figure 73A:
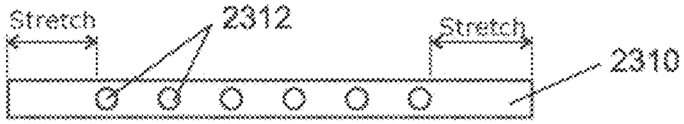
Figure 73B:
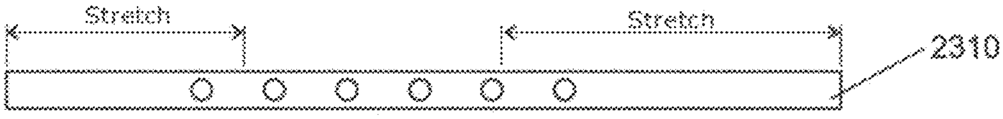
Figure 73C:
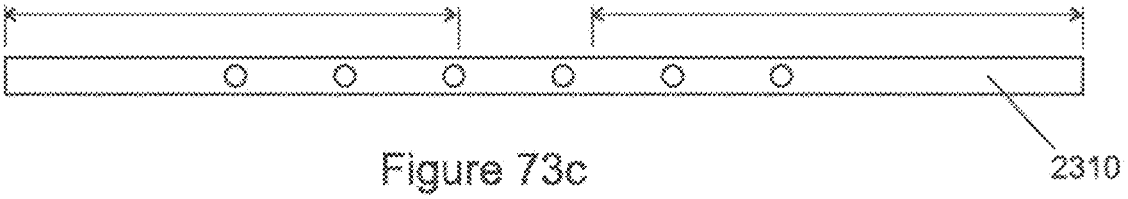
Figure 74:
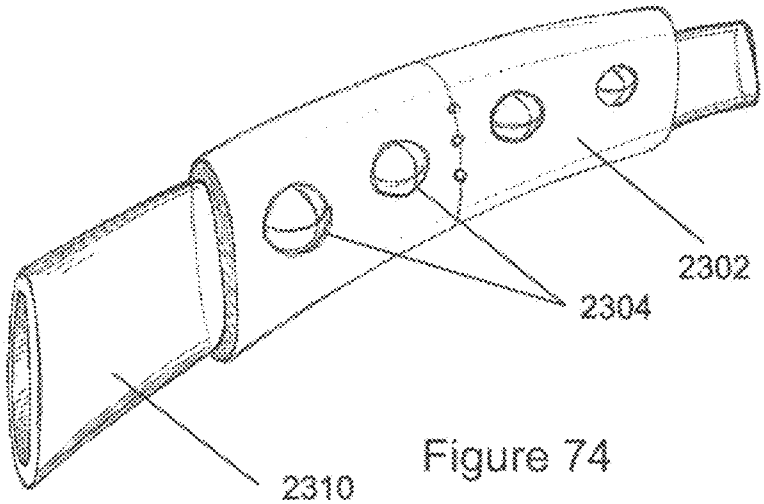
Figure 75:
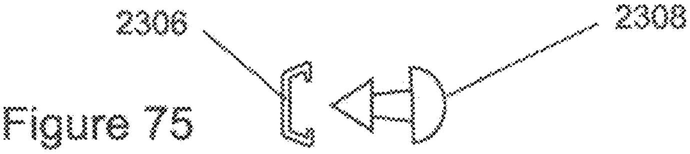
Figure 76:
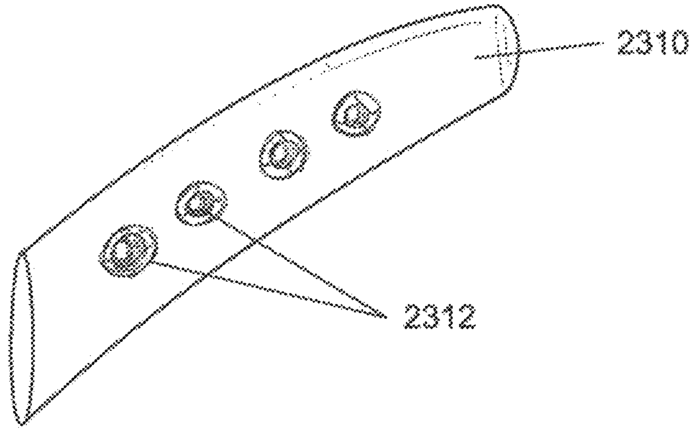
Figure 77:
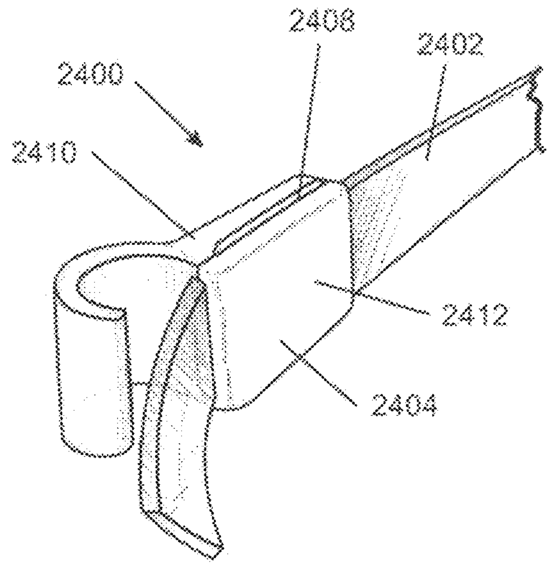
FIGS. 77-81 illustrate headgear incorporating one-time setup features.

In some configurations, such as that shown in FIGS. 73*a*, 73*b*, and 73*c*, the strap 2310 can include predetermined holes 2312 or hole spacing. In some configurations, the holes 2312 of the stretch limiting system 2312 are oversized such that material of the strap 2310 can be displaced into the holes of the stretch limiting system 2300 and secured therein by the button, dome or the like 2304. As described above, the further away from each other the outermost push buttons, domes or the like 2304 are that interlock the relatively non-stretch sleeve 2302 and the relatively stretchable strap 2310, the less of the relatively stretchable strap 2310 is available to stretch.

Figure 72:
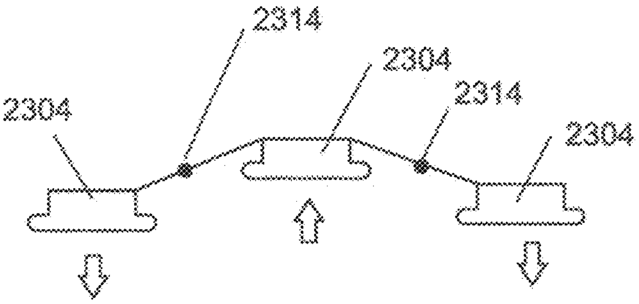

In some configurations, adjacent members, such as adjacent buttons, domes or the like 2304 can be connected by an internal lever release system, such as that shown in FIG. 72. In such configurations, pressing on a first member 2304 can cause movement of two adjacent members 2304. The interconnecting levers can pivot about a hinge point, a fulcrum or the like 2314.

In some configurations, the use of removable buckles, clips, or the like poses problems, such as being bulky, being additional components, and being components that can be broken or lost by the user. Accordingly, incorporating the dome, push buttons, and the like directly into the head gear can be used to remove one or more of these concerns. Built-in buttons also easily can be hidden and/or accounted for in the shaping of the head gear. In other words, the integrated buttons, domes or the like could be recessed in a way that would reduce or eliminate the likelihood of discomfort to the user during use (e.g., when laying on a pillow with the strap between the head and the pillow). In some configurations, the relatively non-stretch sleeve can be secured to the relatively stretchable strap in one or more locations. In some such configurations, the amount of control the relatively stretchable strap will be proportional to the distance from the connection point to the last available button, dome or the like.

Headgear Incorporating One-Time Setup Features

With reference now to FIGS. 77-81, a strap and clip configuration 2400 is illustrated that accommodates one-time set up of a strap 2402 for a headgear assembly.

Figure 78A:
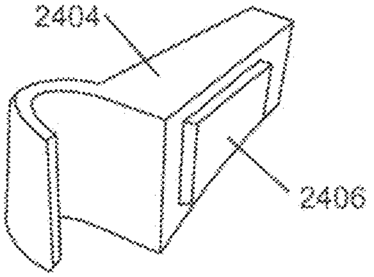
Figure 78B:
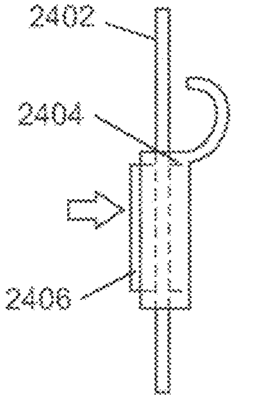
Figure 78C:
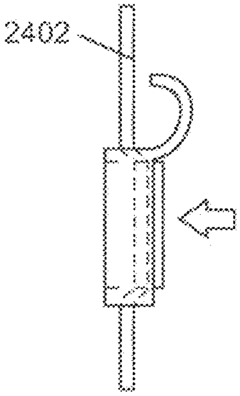
Figure 79A:
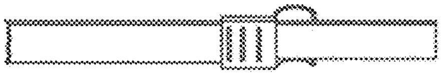
Figure 79B:
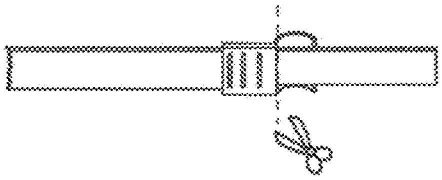
Figure 79C:
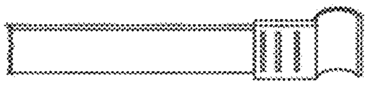
Figure 80:
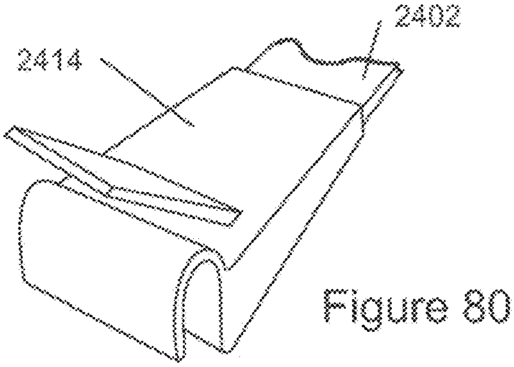
Figure 81:
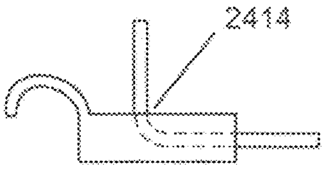
Figure 82:
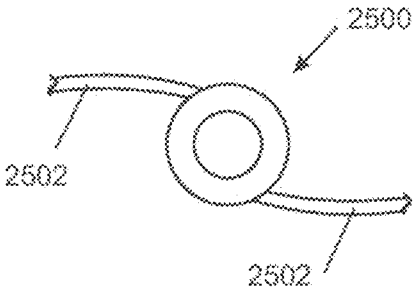
FIGS. 82-87 illustrate an assembly incorporating a screw adjustment for headgear and/or a mask seal.
Figure 83:
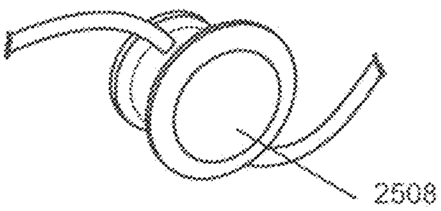

As illustrated, a connector, such as a buckle or clip, 2404 can be configured to attach to a strap 2402. The clip or buckle 2404 can include a passage through which the strap 2402 can be threaded. With reference to FIGS. 78*a*-78*c*, the clip or buckle 2404 also can include a locking member 2406 that can allow the strap to be secured in position. For example, when positioned as shown in FIG. 78*b*, the strap 2402 can be moved through the clip or buckle 2404. When the locking member 2406 is positioned as shown in FIG. 78*c*, the strap 240 can be locked in position relative to the clip or buckle 2404. In some configurations, the strap 2402 can be locked at a specific position permanently.

In some configurations, the head strap 2402 comprises a single strap. In some configurations, the single strap 2402 initially can be provided with excess length to allow the user to feed it through the buckle or clip 2404 to a desired length. Once positioned as desired, the user can cut away the excess, such as with a pair of scissors for example but without limitation. Such a configuration has been illustrated in FIGS. 79*a*-79*c*.

In the some configurations, a living hinge 2408 (see FIG. 77) can be provided between a first portion 2410 and a second portion 2412 of the clip or buckle 2404. The strap 2402 can be positioned between the two portions 2410, 2412 and the two portions can be secured together. With the strap 2402 positioned as desired and the two portions 2410, 2412 locked together, the excess strap can be removed.

In some configurations, the first portion 2410 and the second portion 2412 can be secured together but the strap 2402 can continue to be adjusted. In some configurations, a locking mechanism 2406, such as that described above, can be provided as a part of the buckle or clip 2404. In some configurations, the locking mechanism 2406 can include a push-button that can lock the buckle or clip 2404 in position along the strap 2402. In some configurations, the clip or buckle 2404 can include a hinge system 2414, such as that illustrated in FIGS. 80 and 81. In some configurations, the hinge system 2414 can lock onto the strap 2402 through a pivoting action. In some configurations, the hinge system 2414 allows that strap 2402 to be thread through the buckle or clip 2404 and exposed at a right angle such that the strap 2402 can be more easily trimmed.

By adding in a mechanism that initially allows for excess headgear to be provided and cut away by the user, the aesthetic or function of the single strap head gear can be better maintained while providing adjustability. Further, headgear incorporating one-time setup features may be useful in single-use applications, such as hospital patient treatment, where a single size of headgear may be stocked and fit to patients.

Screw Adjustment for Headgear and/or Mask Seal

With reference now to FIGS. 82-87, some screw adjustment mechanisms 2500 are illustrated that can be used to adjust one or both of the headgear 2502 and the mask seal 2504.

As used herein, a screw adjustment mechanism 2500 can be a mechanism that is positioned at a specific point either on the mask frame 2506 or on the seal component 2504 and that rotates around a central axis to result in adjustments to the fit of the headgear 2502 and/or seal 2504. In the illustrated configurations, the screw adjustment mechanism 2500 may be spring loaded to allow quick and easy retracting/extending of the head strap 2502. In some configurations, the screw adjustment mechanism 2500 could be positioned at one or more adjustment points.

Figure 85:
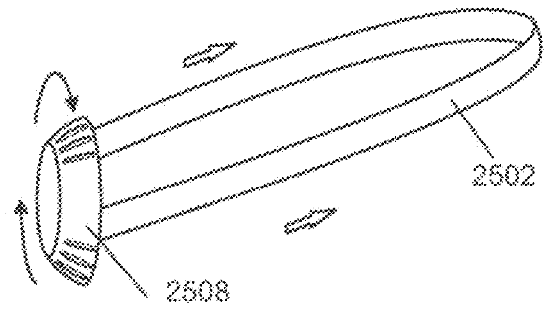
Figure 86:
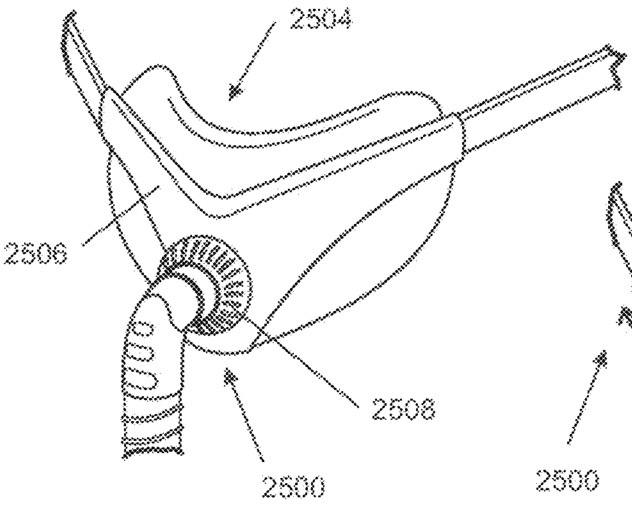
Figure 87:
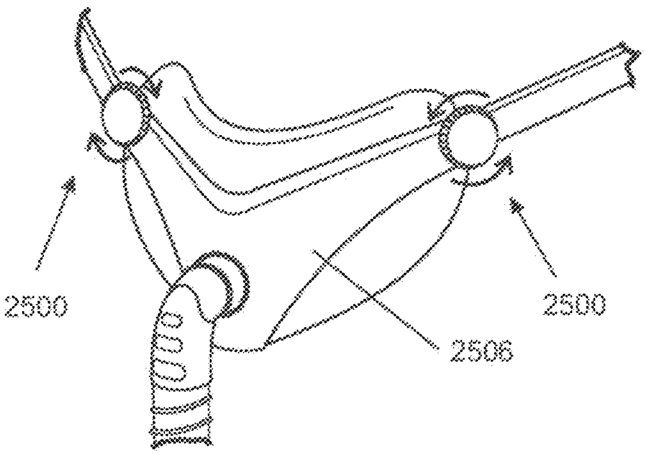
Figure 93:
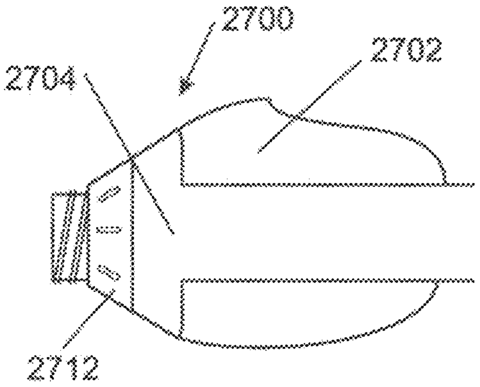
FIGS. 93-98 illustrate an Archimedes screw adjustment for headgear and/or a mask seal.

As used herein, a head strap 2502 is a single or multiple strap head gear that is attached at specific points on the screw mechanism 2500. As the screw mechanism 2500 is turned by the user, the screw mechanism 2500 can wind or unwind the head strap 2502, thereby varying the size of the headgear assembly depending on the user's needs. As shown in FIG. 85, in some configurations, the screw mechanism 2500 can be turned to expand the head strap length and the strap 2502 can be pulled to extract the additional length as desired. In some configurations, a single screw mechanism 2500 can be provided (see, e.g., FIG. 86). In some configurations, multiple screw mechanisms 2500 can be provided (see, e.g., FIG. 87). In some configurations, the screw mechanism 2500 can be provided on each side of the interface.

In some configurations, the screw mechanism 2500 provides a mechanical solution to the adjustability of the single strap head gear 2502. In some configurations, a large dial 2508 (see FIG. 86, e.g.) can be provided directly in front or to the side of the face. The dial 2508 can allow users of all capability levels to easily be able to adjust the head strap to a desired size. For example, the dial 2508 can be twisted to expand or contract the length of the head strap 2502.

Figure 84:
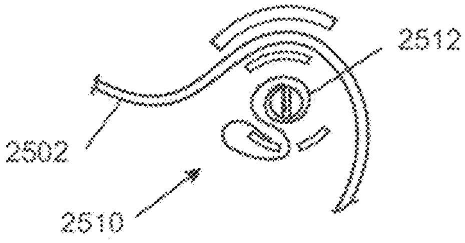

With reference to FIG. 84, in some configurations, a spring-loaded mechanism 2510 can be provided. The spring-loaded mechanism 2510 can have any suitable configuration. In some configurations, the spring-loaded mechanism 2510 can allow the screw mechanism 2500 to self-adjust by simply being over-stretched and the spring 2512 allowed to then retract the strap 2502 into position around the users head. In some configurations, the strap 2502 can lock at certain points and can return to a retracted position upon over extension. Other configurations also can be provided.

Rack and Pinion Adjustment for Headgear and/or Mask Seal

With reference now to FIGS. 88-92, a rack and pinion system 2600 can be provided to adjust the fit of the strap 2602 and/or headgear. In some configurations, the ends of the strap 2602 can be provided with a rack configuration (e.g., teeth) 2604. In some configurations, at least one end of the strap 2602 can be secured to a member that includes teeth and that can serve the function of a rack. In some configurations, a knob 2606 or the like can be provided with teeth that can interlock with the teeth of the rack 2604. By rotating the knob 2606, the length of the strap 2602 can be adjusted.

In some configurations, rather than an actual rack and pinion system 2600 that incorporates meshing teeth, a similar function can be provided through a cord or wire winding mechanism 2608. Such a configuration is shown in FIG. 90. A hook 2610 can be positioned on one or more end of the strap 2602. As the knob 2612 is turned, the length of a cord, wire or the like 2614 can be adjusted and the hook 2610 causes the adjustment to be transferred, at least in part, to the headgear 2602. Other arrangements can be used to secure the headgear 2602 to the cord, wire or the like 2614.

Furthermore, in some configurations, assemblies 2616 can be provided that translate between vertical movement and horizontal movement or between pivotal movement and axial movement of the headgear 2602. In other words, in some configurations, a pivotal movement of a component to which the headgear is attachable can result in an adjustment of the length of the combined headgear and the component. Similarly, in some configurations, movement of one or more component toward each other can result in retraction and extension of the attached headgear. Two such configurations are illustrated in FIGS. 91 and 92. In FIG. 91, one or more pivoting elements 2618 control relative movement between two elements that are connected to the headgear. In FIG. 92, two elements 2620 that move toward and away from each other can cause relative movement between two elements that are connected to the headgear.

Archimedes Screw Adjustment for Headgear and/or Mask Seal

With reference now to FIGS. 93-98, an assembly 2700 is provided that can cause movement of a mask seal 2702 relative to a mask frame 2704, or relative to a headgear assembly 2706, for example but without limitation.

Figure 94:
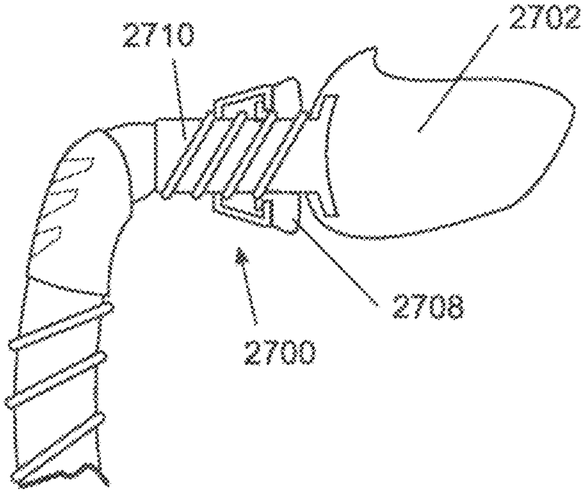
Figure 95:
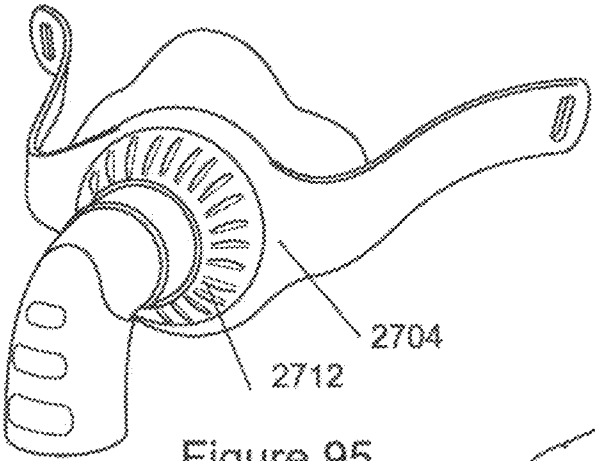
Figure 96:
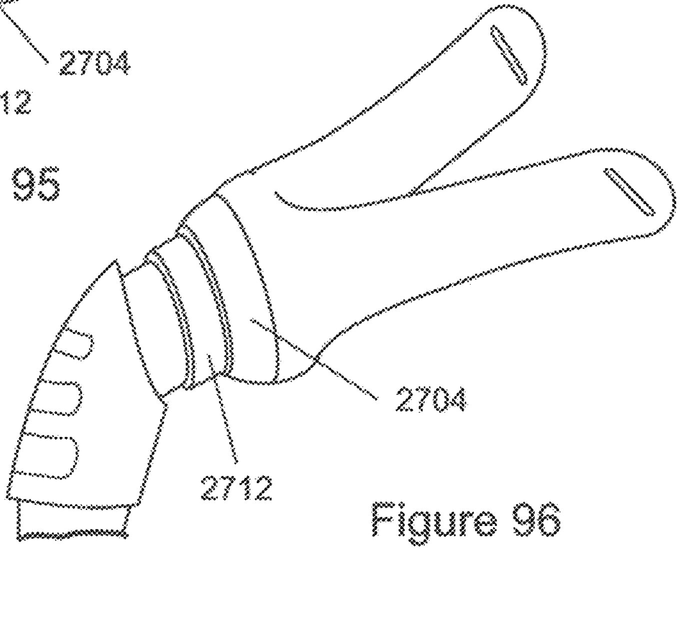
Figure 97:
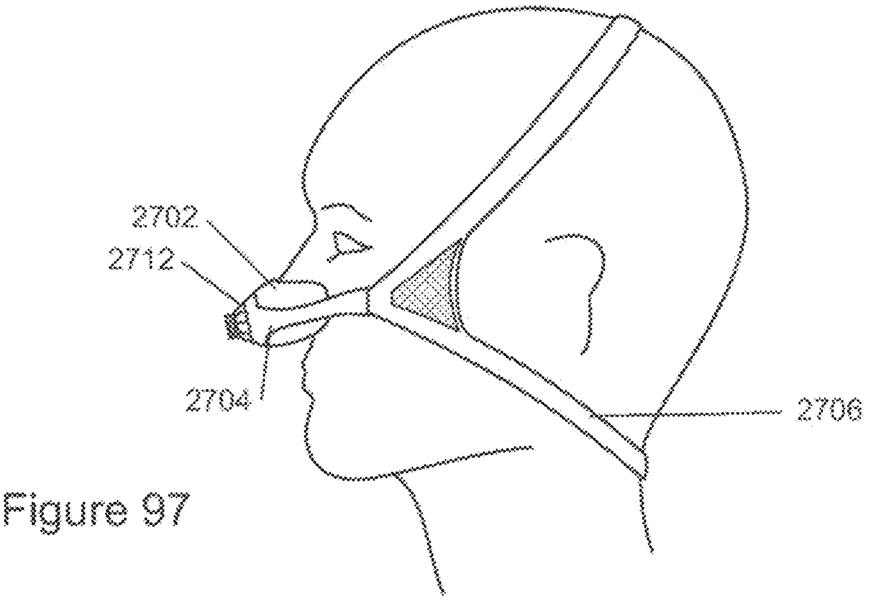
Figure 98:
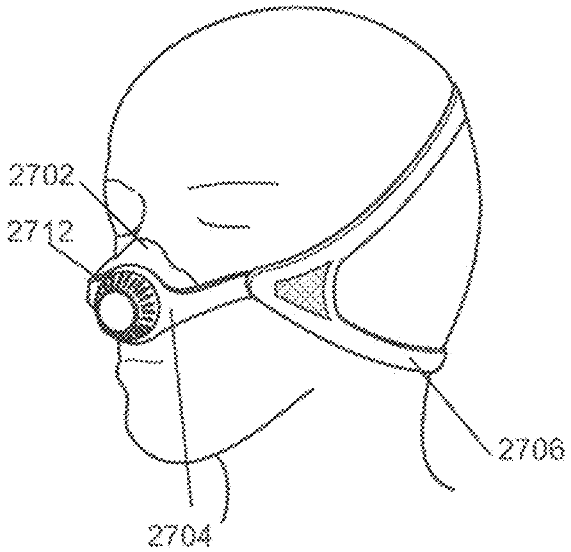
Figure 99:
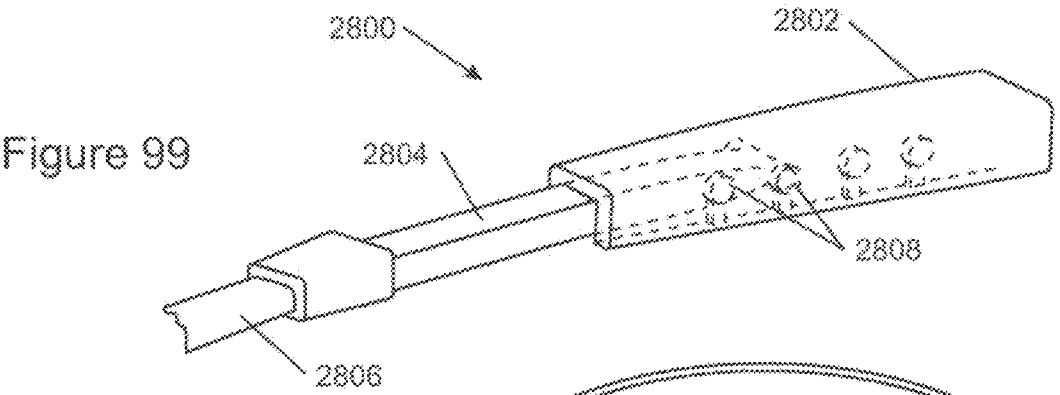
FIGS. 99-102 illustrate an adjustment for headgear and/or a mask seal.
Figure 100:
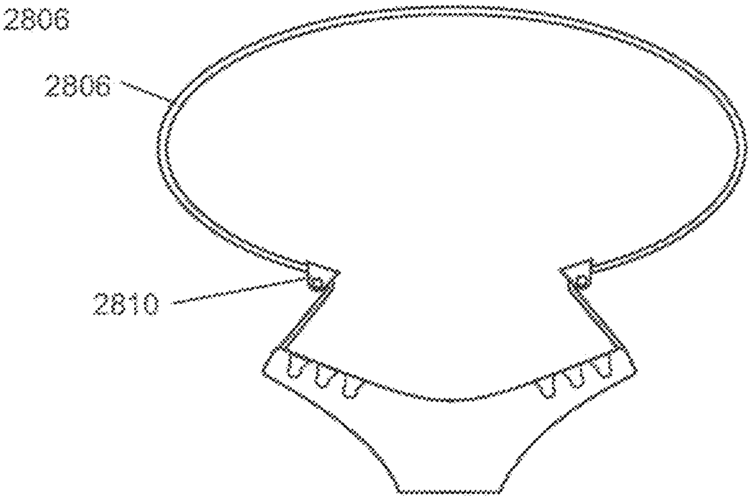

As used herein, a bridge or a bracket 2708 can be a component that creates a predetermined, consistent distance between the users face and the mask/seal 2704/2702. The Archimedes screw 2710 can be attached to the bracket 2708 to provide an adjustment point between the bracket 2708 and the mask seal 2702, as shown in FIG. 94. Advancing and retracting the screw mechanism 2710 directly increases and decreases the force at which the mask seal 2702 is pressing against the users face. The adjustment point can be a ring 2712 that is attached to the Archimedes screw 2710. The ring 2712, when rotated, can advance and retract the screw mechanism or assembly 2700.

Accordingly, because interface designs are designed for the masses, the Archimedes screw mechanism or assembly 2700 can allow fine-tuning of the fit of the interface designs. Thus, more control can be provided for users to adjust the device to better suit their needs or desires.

Snap-On Adjustment for Headgear and/or Mask Seal

With reference now to FIGS. 99-102, a further strap adjustment assembly 2800 is shown. In the illustrated configuration, the strap length can be adjusted by creating a loop with the headgear and then using a suitable assembly to adjust the length of the head strap.

In some configurations, a bracket 2802 can be formed that is attached to the interface or mask assembly while a locking member 2804 can be connected to at least one end of the strap 2806. The bracket 2802 can include a plurality of connecting points 2808 and the locking member 2804 can connect at each of the connecting points 2808; depending upon selected connecting point 2808, the length of the strap 2806 can be adjusted. In such a configuration, a 1:1 adjustment between the strap length and the positioning on the mask frame can result.

Figure 101:
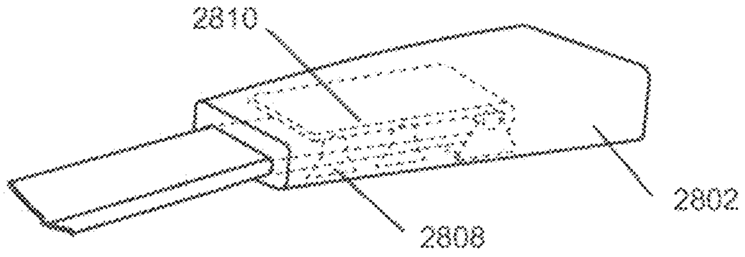
Figure 102:
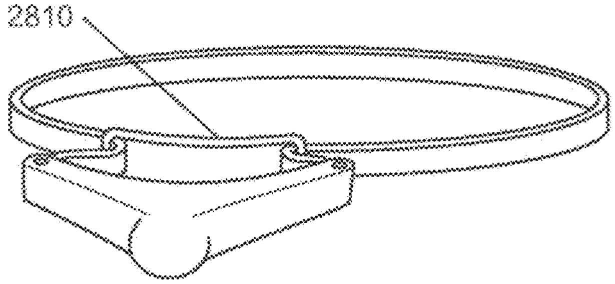
Figure 108:
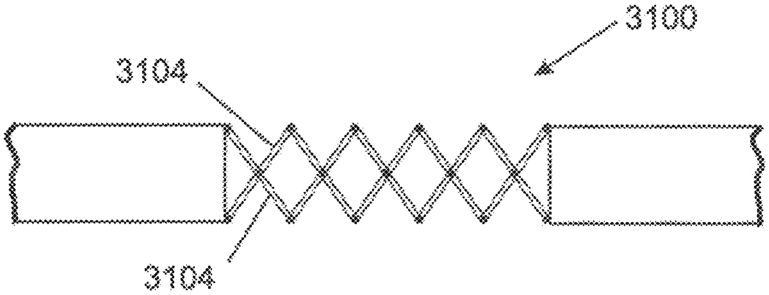
FIGS. 108-110*c* illustrate scissor linkage adjustments for a strap.

In some configurations, such as that shown in FIG. 102, a multiplier 2810, such as a pulley, turnbuckle or the like, can be positioned along the strap 2806 between the ends. In some configurations, such as that shown in FIG. 100, the end connectors for the strap 2806 can have a multiplier 2810 in the form of a hinged structure (e.g., a watch band) with the end being adjustable to adjust the length. As shown in FIG. 101, the hinged structure 2810 can be folded into a receptacle formed in the bracket 2802. In such configurations, the hinged structure 2810 can be secured into one or more of the connecting points 2808 of the bracket 2802. Thus, in such configurations, a smaller adjustment at the frame region can result in a larger adjustment to the headgear strap (e.g., 2:1).

Hook Adjustment for Headgear and/or Mask Seal

With reference to FIG. 103, a strap 2900 can include a small loop 2902 formed at the end. In some configurations, the loop 2902 can be secured to the strap end 2900 with a small fitting 2904. In some configurations, the loop 2902 and strap end fitting 2904 approximate a camera strap.

The mask frame or interface assembly 2906 can include a member with a plurality of hooks 2908. The loop 2902 can be passed over any of the hooks 2908 as desired to provide different levels of adjustment. In some configurations, the hooks 2908 are formed on an inside of the mask. In such configurations, the hooks 2908 and adjustment features are obscured from view, thereby creating a clean look while facilitating an adjustable configuration.

Over-Center Pinch Adjustment for Strap

With reference too FIGS. 104-107*c*, the strap length can be adjusted using an over-center pinch assembly 3000. The figures illustrate a series of mechanisms based on changing the effective length of a strap 3002 by forming a sub-loop 3004 and fixing its position with a clamp 3006. FIG. 104 illustrates a simple folded over strap with an over-center pinch clip used to secure the length of the strap 3002. The strap is secured to the clamp 3006 at a fixing location 3010 FIG. 105 illustrates a construction that is similar to that shown in FIG. 104 but the configuration of FIG. 105 includes a multiplier such that a 2:1 adjustment ratio results. In FIG. 105, the strap 3002 is secured to the mask frame 3012 or the like at a fixing location 3010. Other configurations also are possible.

FIGS. 106 and 107*a*-107*c* illustrate a continuous loop headgear 3014. To adjust the effective length of the headgear, a sub loop 3016 is formed and folds back on itself. The position can be fixed with any suitable clamp 3018, for example. In some configurations, the clamp 3018 can be an over center clamp. FIGS. 107*a*-107*c* illustrate the effect of using various sizes of sub loops 3016 on the overall headgear size.

Scissor Linkage Strap Adjustment

With reference now to FIGS. 108 through 110*c*, a scissor link system 3100 is illustrated. The scissor link system 3100 can comprising a plurality of matched sets of pivoting arms 3104. Both of the arms of each set can be linked together and each of the sets can be linked together. Other configurations are possible.

Figure 109A:
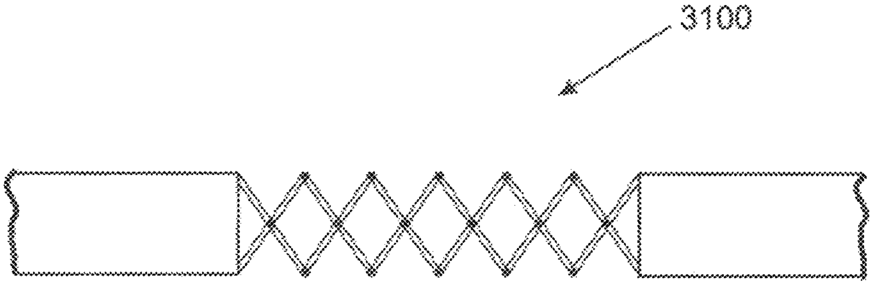
Figure 109B:
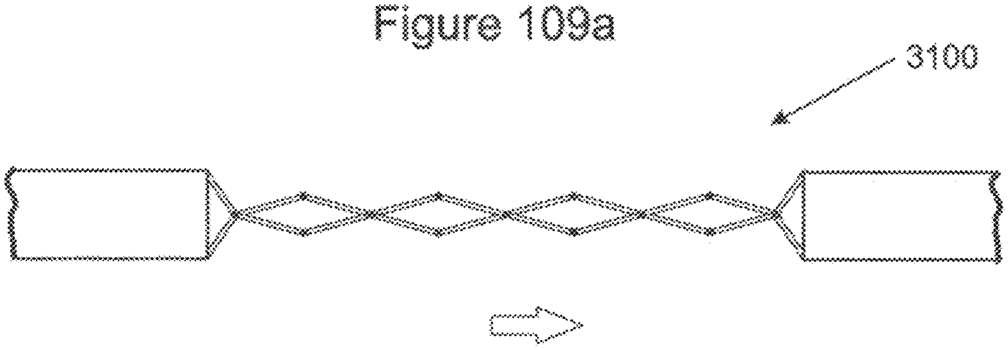
Figure 109C:
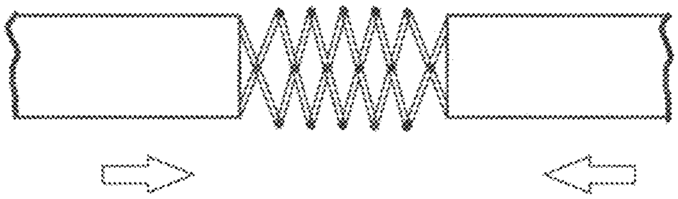

The scissor link system 3100 allows varying degrees of adjustability based on whether the links have been expanded or contracted, as illustrated in FIGS. 109*a*-109*c*. It is envisaged that this could be a large mechanical type mechanism, or could be scaled down much further to the point where the device functions the same but may not be apparent to the naked eye how this works.

Figure 110A:
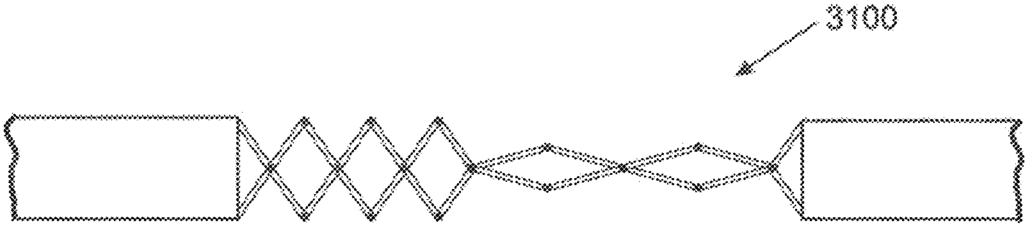
Figure 110B:
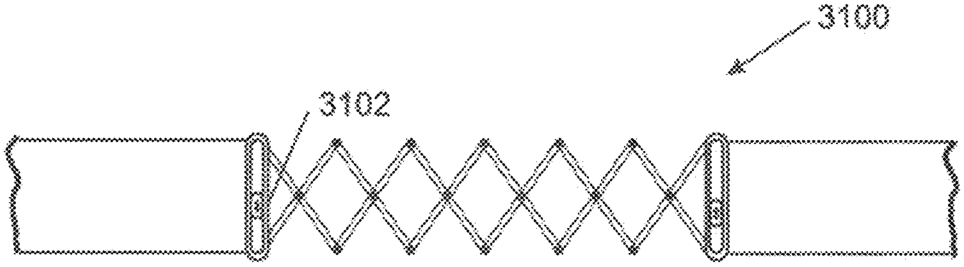
Figure 110C:
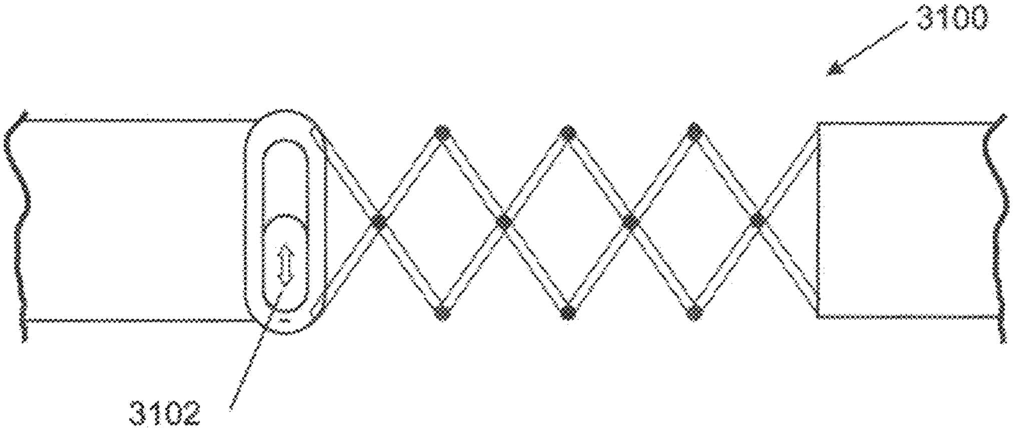
Figure 111:
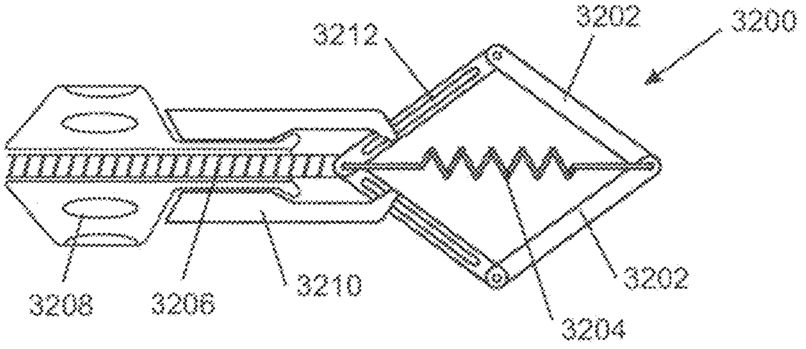
FIGS. 111-114 illustrate a fine-tuning adjustment for a scissor linkage for a strap.
Figure 112:
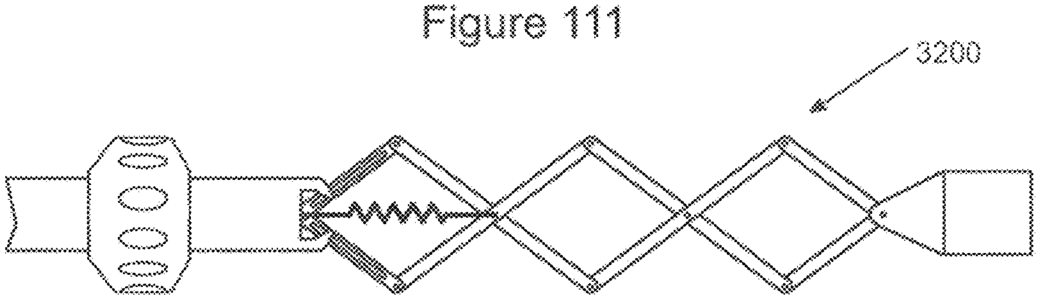
Figure 113:
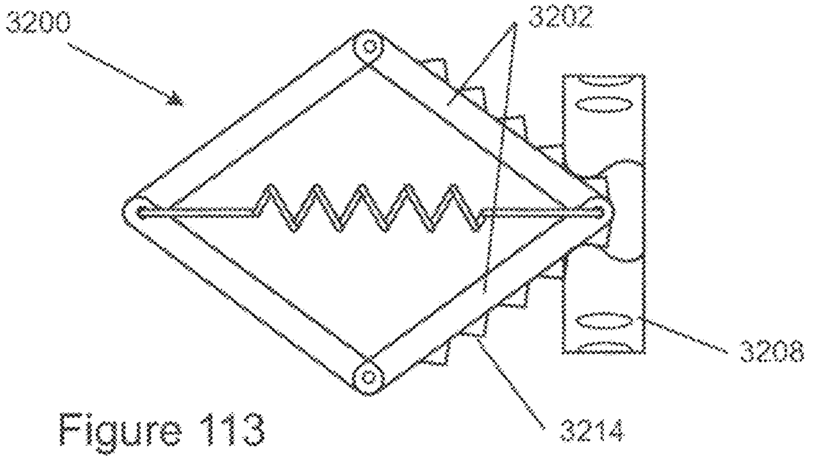
Figure 114:
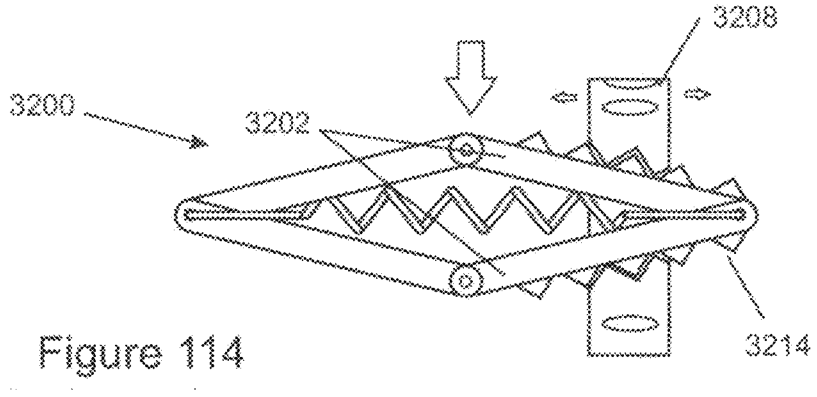

In some configurations, the scissor link system 3100 includes an adjustment mechanism 3102, as shown in FIGS. 110*b*, 110*c*. The adjustment mechanism 3102 can include a button or a glider that, when adjusted, will directly affect the level of compression or extension in the scissor link system 3100. Because of the mechanical nature of the adjustment, there is much greater control over the amount of adjustment, the ease of adjustment and the strength of materials compared to the configurations discussed above.

In some configurations, the adjustment mechanism 3102 and the scissor link system 3100 is configured such that each of the scissor arms will experience a generally equal adjustment throughout the assembly 3100. In some configurations, however, different sections of the assembly 3100 can be adjusted with different degrees of expansion or compression. For example, as shown in FIGS. 110*a* and 110*b*, one end may remain generally compressed while the other end may be more fully expanded.

In some configurations, such as that shown in FIG. 110*c*, the scissor link system 3100 can include a member 3102 that allows for the adjustment to be locked. In some configurations, the adjustment member (or locking member) 3102 can be positioned at each end of the scissors mechanism (e.g., FIG. 110*b*). In some configurations, the adjustment member (or locking member) 3102 can be positioned at only one end (e.g., FIG. 110*c*). In some configurations, the adjustment member (or locking member) can be used to adjust one linkage, which can result in adjustment to the rest of the linkages. In some configurations, the adjustment member (or locking member) can be a push-button or the like. Other configurations are possible.

Fine Tuning Adjustment for Scissor Link

With reference now to FIGS. 111-114, several additional scissor link systems 3200 are shown. The illustrated configurations provide for more finely tuned adjustments.

As described above, a scissor link system 3200 allows varying degrees of adjustability based on whether the links 3202 have been expanded or contracted. In some configurations, one or more of the links 3202 can be biased using a spring 3204 or another suitable biasing member. In some such configurations, an extension spring 3204 can apply a force (e.g., a constant force) on the scissor links 3202 in order retract the links 3202 as and when required or desired by the user.

In some configurations, a threaded member 3206 can be used in order to expand or contract the links 3202 via the twist knob or push button 3208. In such configurations, for example, a bracket 3210 can be used to maintain a distance between the threaded member 3206, the associated link 3202 and one or more tracks 3212. As used herein, tracks 3212 can be slots, grooves, protrusions or that like that can be formed on or the scissor links 3202, which, in combination with the bracket 3210 and threaded member 3206, allow the links 3202 to smoothly retract and expand. In some configurations, movement of the threaded member 3206 can be directed using a twist knob 3208 or the like. For example, in some configurations, the knob 3208 or button can be used to twist, push or pull the threaded member 3206 forward and backward, which results in the scissor links 3202 expanding and retracting. Other suitable configurations also can be used. For example, in some configurations, such as that illustrated in FIGS. 113 and 114, an external thread 3214 can generally enclose two of the links 3202 or the links 3202 can have a threaded surface 3214. In such configurations, turning the knob 3208 causes the knob 3208 to advance along the links 3202 and to compress the links 3202 toward each other (because the internally threaded portion of the knob 3208 does not change sizes).

The illustrated configurations provide greater control over the level of adjustment to the headgear via the scissor link system 3200. In some configurations, a visual indicator can be provided showing a specific setting (e.g., 1-10). The visual indicator would allow users to quickly and easily set up the head gear after cleaning and/or would allow users to match existing settings when they replace the head gear in the future.

Adjustment for Headgear and/or Mask Seal

With reference now to FIGS. 15-16*h*, an arrangement featuring a hook and loop fastener based limiting/locking system 3300 is illustrated. As used herein, a hook tab 3302 is a tab specifically designed to increase the difficulty of removing the strap 3304 in question. This system 3300 provides adjustment to users who are trained in its use and makes it more difficult for users who are not. As used herein, a loop head strap 3304 means a loop material for the hook 3302 to grab onto and lock in place.

In some headgear configurations, the headgear can require a one-time set up by a sleep tech or other experienced person. Following the one-time set up, it is intended that such headgear not be readjusted by the user. The one-time set up poses a problem in how to create a method of adjustment that can be adjusted by one person but not another. By utilizing a more complex adjustment method such as the hook tab 3302 proposed, trained/experienced users will easily be able to make the adjustment, while the difficulty in doing so for others not trained will deter them from using it and instead direct them to use other adjustment methods provided.

In some configurations, the hook tab 3302 comprises a forked configuration with at least one recessed region 3306. In some such configurations, the hook tab 3302 comprises a plurality of fingers 3308. The plurality of fingers 3308 need to be raised simultaneously in order to release the hook tab 3302 from the underlying loop material of the strap 3304, for example but without limitation. A variety of tab configurations are illustrated in FIGS. 115 and 116*a*-116*i*. In many of the configurations, one or more of the fingers 3308 extends further along the strap 3304 than others of the fingers. In some of the configurations, one or more of the fingers 3308 is at least partially circumscribed by another of the fingers 3308. In some of the configurations, one or more of the fingers 3308 is fully circumscribed by another of the fingers 3308. In some configurations, for example, FIG. 116*i*, the fingers are not circumscribed but, rather, the hook tab 3303 comprises a wide free end 3310 connected to a second portion 3312 via a narrow section 3314 with the fingers 3308 being located on one or both sides of the narrow section 3314 having fingers 3308 on either or each side.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use by a patient or user. However, certain features, aspects and advantages of the use of the headgear and/or straps as described may be advantageously practiced by other people on behalf of the patient, including medical professionals, medical device dealers, or medical device providers. Certain features, aspects and advantages of the methods and apparatus of the present disclosure may be equally applied to usage by other people.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

The invention claimed is:

1. A headgear assembly for use with a patient interface, the headgear assembly comprising:

at least one strap configured to be secured to the patient interface, the at least one strap comprising an end with a hook tab;

the hook tab being securable to a loop material of the strap;

the hook tab comprising at least two fingers that are spaced apart from each other by a gap such that one of the at least two fingers can be lifted without lifting of another of the at least two fingers.

2. The headgear assembly of claim 1, wherein the at least two fingers are symmetrical with each other.

3. The headgear assembly of claim 1, wherein the at least two fingers are asymmetrical with each other.

4. The headgear assembly of claim 1, wherein the gap results in the at least two fingers defining a forked configuration.

5. The headgear assembly of claim 1, wherein the gap is centrally positioned along the hook tab.

6. The headgear assembly of claim 1, wherein said one of the at least two fingers at least partially circumscribes said another of the at least two fingers.

7. The headgear assembly of claim 6, wherein said one of the at least two fingers fully circumscribes said another of the at least two fingers.

8. The headgear assembly of claim 7, wherein said one of the at least two fingers defines a central tab and said another of the at least two fingers defines an outer tab that circumscribes the central tab.

9. The headgear assembly of claim 1, wherein said one of the at least two fingers only partially circumscribes said another of the at least two fingers.

10. The headgear assembly of claim 1, wherein the gap extends inwardly from a lateral edge of the hook tab.

11. The headgear assembly of claim 1, wherein a second gap extends inwardly from a second lateral edge of the hook tab and the at least two fingers are defined with a narrow section connecting to a wide end.

12. The headgear assembly of claim 1, wherein said one of the at least two fingers extends further along the strap than said another of the at least two fingers.

13. The headgear assembly of claim 1, wherein the hook tab further comprises a wide free end connected to a second portion via a narrow section.

14. The headgear assembly of claim 13, wherein the at least two fingers are located on one side of the narrow section.

15. The headgear assembly of claim 13, wherein said one of the at least two fingers is located on a first side of the narrow section, and said another of the at least two fingers is located on a second side of the narrow section.

16. The headgear assembly of claim 1, wherein the at least two fingers are configured to be secured to a same side of the strap.

17. The headgear assembly of claim 1, further comprising a connector clip, wherein the at least one strap is configured to be secured to the patient interface by the connector clip.

18. The headgear assembly of claim 1, wherein the hook tab comprises an attachment end that is attached to the end of the strap, wherein at least a portion of each of the at least two fingers defines a width that is less than a width of the attachment end of the hook tab.

19. A headgear assembly for use with a patient interface, the headgear assembly comprising:

at least one strap configured to be secured to the patient interface, the at least one strap comprising an end with a hook tab, the hook tab being securable to a loop material of the strap;

the hook tab comprising at least two fingers that are spaced apart from each other by a gap, wherein the at least two fingers are configured to be secured to a same side of the strap.

20. The headgear assembly of claim 19, wherein each of the at least two fingers has a tip, wherein the tip of one of the at least two fingers can be lifted from the strap separately from the tip of another of the at least two fingers.

* * * * *